United States Patent [19]

Moren et al.

[11] Patent Number: 5,149,806
[45] Date of Patent: Sep. 22, 1992

[54] AZLACTONE MICHAEL ADDUCTS

[75] Inventors: Dean M. Moren, North St. Paul; Steven M. Heilmann, Afton; Larry R. Krepski, White Bear Lake; Jerald K. Rasmussen, Stillwater, all of Minn.

[73] Assignee: Minnesota Mining and Manufacturing Company, St. Paul, Minn.

[21] Appl. No.: 500,768

[22] Filed: Mar. 28, 1990

[51] Int. Cl.⁵ .......................................... C07D 265/06
[52] U.S. Cl. ...................................... 544/72; 544/96; 544/97
[58] Field of Search ................. 544/71, 96, 90, 89, 544/92

[56] References Cited

U.S. PATENT DOCUMENTS

| | | | |
|---|---|---|---|
| 3,694,417 | 9/1972 | Rigby et al. | 260/78 UA |
| 4,092,298 | 5/1978 | Humbert et al. | 260/75 T |
| 4,266,040 | 5/1981 | Lin | 521/90 |
| 4,291,152 | 3/1980 | Inata et al. | 528/289 |
| 4,485,236 | 11/1984 | Rasmussen et al. | 544/69 |
| 4,639,286 | 1/1987 | Rasmussen et al. | 156/307.3 |
| 4,785,070 | 11/1988 | Rasmussen et al. | 528/73 |

FOREIGN PATENT DOCUMENTS 887530 11/1941 France.

OTHER PUBLICATIONS

*J. Am. Chem. Soc.*, 77, 1541–1543, "Polyamides from 2,2'-Bis-[5(4H)-oxazolones], ", Cleaver et al., (1955).
*Enc. Pol. Sci. & Eng.*, 2nd Ed., vol. 11, 1988, pp. 558–571, Rasmussen et al., "Polyazlactones".

*Primary Examiner*—Nicholas S. Rizzo
*Attorney, Agent, or Firm*—Gary L. Griswold; Walter N. Kirn; Lorraine R. Sherman

[57] ABSTRACT

Azlactone-functional Michael adducts are disclosed which are the Michael reaction products of 2-alkenyl azlactones and Michael donors selected from carbon and nitrogen nucleophiles. Reaction products which contain a plurality of azlactone groups are useful as step growth monomers in adhesives, sealants, and coatings.

13 Claims, No Drawings

AZLACTONE MICHAEL ADDUCTS

FIELD OF THE INVENTION

This invention relates to novel azlactone-functional Michael adducts and to a method of preparation thereof. Multi-azlactone compounds find use as step growth monomers for polymers used in adhesives, sealants, and coatings.

BACKGROUND OF THE INVENTION

Isocyanate-derived polymers such as polyurethanes and polyureas have been workhorse materials in the automotive, furniture, carpet, construction, sporting goods, and packaging industries for many years. Production of these materials in foam, molding, casting, coating, and film forms presently exceeds two billion tons annually. Utilization of bis(isocyanates) as step growth monomers began in Germany in the 1930's and became industrially important primarily for the following reasons: 1) their derived polymers possessed unique and outstanding properties; 2) the synthesis of the isocyanate monomers by the phosgenation of aromatic amines was relatively inexpensive and conducive to large-scale manufacture; and 3) isocyanates react with alcohol and amine nucleophiles at high rates by nucleophilic addition in which no smaller molecule is generated that must be removed from the system.

Yet, despite their virtual ubiquitous application in our present day technology, some significant problems attend isocyanates and their polymers. An important problem is toxicity of both the isocyanates and amines derived from their hydrolysis and from their polymers. Isocyanate monomers have long been known to be exceedingly hyperallergenic, often causing permanent sensitization and serious health problems. Furthermore, the hydrolysis product of one of the most important poly(isocyanate) monomers, 2,4-toluenediisocyanate (TDI), is listed by the World Health Organization among the "chemicals which are probably carcinogenic for humans". This is reflected by the very low threshold limit value for most diisocyanates at 5 parts per billion on a time-weighted average over an 8 hour period. With the increased public consciousness about chemical pollution, this toxicity has led some European countries to presently prohibit the sale and use of new products containing poly(isocyanate) materials within their borders.

Aside from very significant toxicity issues, the high degree of reactivity of isocyanates has given rise to some practical problems in their application. Packaging of poly(isocyanates) must be scrupulously anhydrous, as water reacts to form unstable carbamic acids and finally amines. Reaction of these amines and residual isocyanate groups can then result in a prematurely crosslinked, useless material. Another problem is that the isocyanate groups can self-condense forming dimers and trimers. In the extreme these can result in undesirable crosslinking as discussed above, and even when occurring to a lesser extent, the self-condensation results in chain extension to an undefined extent. The precise isocyanate concentration is no longer known, and the stoichiometry which is critically important in step growth polymerizations is rendered a guessing game. A still further problem is that isocyanate groups are so reactive that they can engage in reaction with urethane and urea product linkages forming allophanate and biuret linkages, respectively. These reactions often result as well in undesirable, uncontrolled crosslinking.

Although epoxy-based systems have enjoyed relatively widespread industrial usage, nucleophilic additions to epoxies by alcohols and amines proceed at significantly slower rates than isocyanate systems. This is reflected in the conditions for cure of a typical two-package epoxy/amine structural adhesive requiring temperatures in excess of 15° C. (60° F.) for 18-24 hours. Furthermore, the epoxy systems are not without other problems and typically do not constitute an effective replacement for isocyanate-based polymers.

Azlactones (2-oxazolin-5-ones) have been known since the last century and would seem to offer features similar to isocyanates as well as some distinct advantages. The azlactone heterocycle reacts with nucleophiles by a similar addition reaction as the isocyanates resulting in ring-opened products. Furthermore, hydroxy and amine nucleophiles are reactive with azlactones, and the same commercial polyol and polyamine comonomer materials used with poly(isocyanates) can be used with poly(azlactones). As far as advantages, the azlactone offers significantly improved resistance to hydrolysis, i.e., ring-opening with water, and even if hydrolysis does occur due to prolonged exposure to moisture, the amidoacid hydrolysis products are not reactive with residual azlactones. Therefore, packaging and shelf stability of poly(azlactones) would not be the significant problems they are with poly(isocyanates). Another advantage of azlactone-based systems is in regard to uncontrolled crosslinking. The azlactones are not as highly reactive with nucleophiles as are especially the aromatic isocyanates which are the most common poly(isocyanates) employed. Consequently, control of reaction conditions and product linkages can be more easily achieved. Azlactones are not reactive with amide or ester product linkages and uncontrolled crosslinking does not occur in the fashion of isocyanate-urethane (allophanate) and -urea (biuret) reactions.

Utilization of bis(azlactones) as step-growth monomers was first disclosed in French Patent 887,530. Although the polymers were not well characterized, soluble, fiber-forming polyamides and polyesteramides were described, as was the use of bis(azlactones) as crosslinkers for cellulose acetate, poly(vinyl acetals), and casein. In a later more detailed study (*J. Am. Chem. Soc.*, 77, 1541 (1955)), several bis(azlactones) were reacted with aliphatic diamines, aromatic diamines, and N-substituted aliphatic diamines. Solution polymerization provided semi-crystalline polyamides of variable molecular weight. Poly(2-imidazolin-5-ones) were provided by a variation of the reaction in which diamines containing basic groups or when certain added catalysts were utilized as disclosed in in U.S. Pat. No. 4,785,070. Heating at 180°-200° C. caused formation of catenary 2-imidazolin-5-one units via intrapolymeric cyclodehydration.

Bis(azlactones) have also been utilized as additives to hydroxy-functional polymers to increase performance in powder coatings (See U.S. Pat. No. 4,092,298) and in aromatic polyesters (See U.S. Pat. No. 4,291,152).

Bis(azlactones) which contain hydrogen substituents in the 4,4'-positions are mesionic and possess 1,3-dipolar character. This has been exploited to form polymers by cycloaddition reactions with electron deficient olefins as disclosed in U.S. Pat. Nos. 3,694,417 and 4,266,040.

Many of the applications of poly(isocyanates) require that materials be fluid at room temperature. What has probably contributed to the greatest extent to the more limited use of poly(azlactones) is that, with a few exceptions vide infra, the many reported bis(azlactones) are high melting solids. Table 1 of a review entitled "Polyazlactones" by J. K. Rasmussen, et al., *Encyclopedia of Polymer Science and Engineering*, Second Edition, Volume 11, 1988, pp.558-571 contains a listing of reported bis(azlactones) and their melting points and is incorporated herein by reference.

Two classes of azlactone-functional compounds that typically are fluids at room temperature are disclosed in U.S. Patent Nos. 4,485,236 and 4,639,286. These two classes of azlactone compounds result from 1) the uncatalyzed Michael addition of highly nucleophilic secondary amine compounds to the β-carbon of the alkenyl group of 2-alkenyl azlactones and 2) the acid-catalyzed Michael addition of thiol compounds to the same group of 2-alkenyl azlactones. These azlactone-functional reaction products differ compositionally and generally differ in method of preparation from the compositions and method of the present invention.

SUMMARY OF THE INVENTION

Briefly, this invention provides novel azlactone-functional compounds which are Michael reaction products of selected Michael donors to 2-alkenyl azlactone Michael acceptors. Michael donor compounds useful in the present invention are carbon nucleophiles and weakly basic nitrogen nucleophiles.

In another aspect, this invention provides a novel process for the preparation of azlactone-functional compounds in which basic catalysts (and/or catalysts which are capable of creating a base in situ) are employed.

In yet another aspect, this invention provides novel monoazlactone compounds that can react or couple with polymers, and multi(azlactone) compounds that can be used as step growth monomers for employment with polyol and polyamine monomers in two-part package adhesives, sealants, and coatings.

In this application:

"alkenyl" and "alkenylene" mean the monovalent and polyvalent residues remaining after removal of one and at least two hydrogen atoms, respectively, from an alkene containing 2 to 20 carbon atoms; functional groups which may be present are one or more aryl, amide, thioamide, ester, thioester, ketone (to include oxo-carbons), thioketone, nitrile, nitro, sulfide, sulfoxide, sulfone, disulfide, tertiary amine, ether, urethane, dithiocarbamate, quaternary ammonium and phosphonium, halogen, silyl, silyloxy, and the like, wherein the functional groups requiring substituents are substituted with hydrogen, alkyl, or aryl groups where appropriate; additionally, the alkenyl and alkenylene residues may contain one or more catenary S, O, N, P, and Si heteroatoms;

"alkyl" and "alkylene" mean the monovalent and polyvalent residues remaining after removal of one and at least two hydrogen atoms, respectively, from a linear or branched chain hydrocarbon having 1 to 20 carbon atoms, functional groups and catenary heteroatoms which may be present are the same as those listed under the "alkenyl" definition;

"aryl" and "arylene" mean the monovalent and polyvalent residues remaining after removal of one and at least two hydrogen atoms, respectively, from an aromatic compound (single ring and multi- and fused-cyclic) having 5 to 12 ring atoms in which up to 5 ring atoms may be selected from S, Si, O, N, and P heteroatoms, functional groups which also may be present are the same as those listed under the "alkenyl" definition;

"azlactone" means 2-oxazolin-5-one groups of Formula I and 2-oxazin-6-one groups of Formula II;

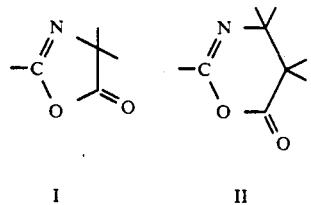

I   II

"cycloalkyl" and "cycloalkylene" mean the monovalent and polyvalent residues remaining after removal of one and at least two hydrogen atoms, respectively, from a cyclic hydrocarbon having 3 to 12 ring atoms of which one or more of the ring atoms may be N, O, S, P, and Si atoms and functional groups listed under the "alkenyl" definition may also be present;

"lower alkyl" means C-1 to C-4 alkyl;

"Michael reaction" means the catalyzed or uncatalyzed addition of a "Michael donor", illustrated by a carbon nucleophile (III) in the equation below, to an alkenyl azlactone "Michael acceptor" (IV) to form a "Michael adduct" reaction product (V);

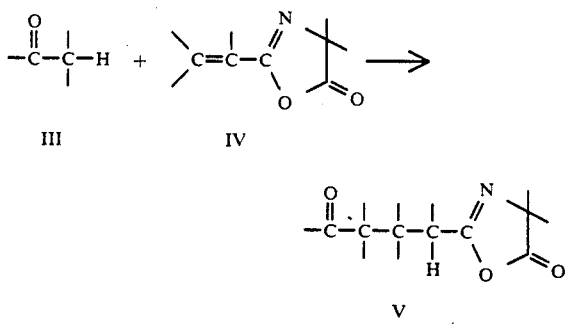

and

"Michael donor" means the nucleophilic reactant in a Michael reaction;

"Michael acceptor" means the electrophilic reactant in a Michael reaction;

"substantially perfluorinated" means hydrocarbon groups in which at least 50 percent, preferably at least 85 percent, and more preferably 100 percent, of the hydrogen atoms have been replaced by fluorine, and one or more heteroatoms of N, O, S, P, and Si may be present.

DETAILED DESCRIPTION OF THE INVENTION

The present invention provides novel Michael adducts having Formula VI:

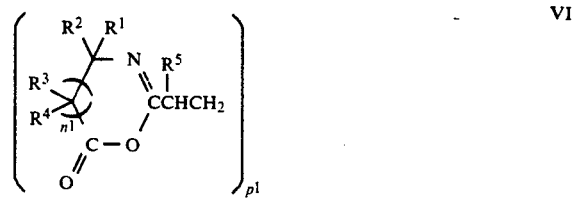

-continued

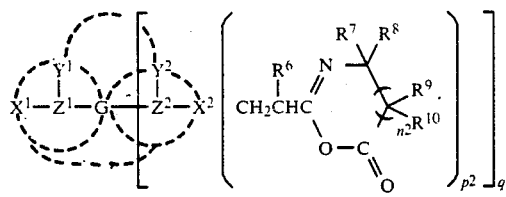

wherein $p^1$ and $p^2$ independently can have integral values of 1 to (the valence of $X^1$ or $X^2$) - 1, and $p^1$ relates to $X^1$ and $p^2$ to $X^2$;

$R^1$, $R^2$, $R^7$, and $R^8$ independently can represent an alkyl group, a cycloalkyl group, an aryl group, or at least one of ($R^1$ and $R^2$) and ($R^7$ and $R^8$) taken together with the carbon atom to which they are joined forms a ring of 4 to 12 atoms;

$R^3$, $R^4$, $R^9$, and $R^{10}$ are independently hydrogen or lower alkyl;

$R^5$ and $R^6$ independently are hydrogen or methyl;

$n^1$ and $n^2$ independently are 0 or 1;

$X^1$ and $X^2$ independently can be selected from the group consisting of —$CH_2$ (when at least one of $p^1$ and $p^2=1$); —CH (when at least one of $p^1$ and $p^2=2$); —C (when at least one of $p^1$ and $p^2=3$); —$CR^{11}R^{12}$ in which $R^{11}$ and $R^{12}$ are selected from the group consisting of alkyl, alkenyl, cycloalkyl, and aryl monovalent groups, a single bond, and polyvalent alkylene, alkenylene, cycloalkylene, and arylene linking groups; —$CHR^{11}$; —$CR^{11}$; —$CW^1W^2$ in which $W^1$ and $W^2$ are independently selected from $R^{11}O_2C$—, $R^{11}(CO)$—, $N\equiv C$—, $R_F(CO)$— in which $R_F$ is a substantially perfluorinated alkyl, cycloalkyl, or aryl group, $R^{11}NH(CO)$—, $R^{11}R^{12}N(CO)$—, $R^{11}SO_2$—, $R^{11}R^{12}C=N$—, $R^{11}N=(R^{12})C$—, $R^{11}(CS)$—, $R^{11}S_2C$—, $R^{11}NH(CS)$—, $R^{11}R^{12}N(CS)$—, $R^{11}R^{12}C=CR^{13}$ — (in which $R^{13}$ can be defined the same as $R^{11}$ and $R^{12}$), and $O_2N$— groups; —$CR^{11}W^1$; —$CHW^1$; —$CW^1$; —$NR^{14}$ in which $R^{14}$ (linking at least one of $X^1$ to $Y^1$, $X^1$ to G, $X^1$ to $X^2$, $X^2$ to $Y^2$, and $X^2$ to G) is a single bond, alkylene, alkenylene, or arylene group such that the ring formed contains 4 to 6 ring atoms; and —$NW^1$;

$Z^1$ and $Z^2$ independently can be C, N, or S=O;

$Y^1$ and $Y^2$ independently can be doubly bonded oxygen (=O); doubly bonded sulfur (=S); =$CR^{15}R^{16}$ in which $R^{15}$ and $R^{16}$ independently can be defined the same as $R^{11}$, $R^{12}$, and $R^{13}$, except that $R^{15}$ can be an electron pair; —$CR^{15}=CR^{16}R^{17}$ in which $R^{17}$ can be a monovalent group selected from alkyl, alkenyl, cycloalkyl, and aryl groups; =$NR^{15}$ [to include triply bonded nitrogen (≡N:) when $R^{15}$ is an electron pair and G is a single bond from $Y^1$ to $Z^1$ (and/or $Y^2$ to $Z^2$)]; —$NR^{18}R^{19}$ in which $R^{18}$ and $R^{19}$ independently can be hydrogen, alkyl, cycloalkyl, aryl, a single bond, alkylene, cycloalkylene, and arylene or together with the nitrogen atom to which they are joined form a ring of 4 to 12 ring atoms;

G can be —H; —$NR^{20}R^{21}$ in which $R^{20}$ and $R^{21}$ independently can be defined the same as $R^{11}$, $R^{12}$, and $R^{13}$; —$NHR^{20}$; —$R^{20}$; —$OR^{20}$; =O; and polymeric monovalent and polyvalent groups; an electron pair; a single bond; G can contain one or more of S, O, N, P, halogen, and Si atoms; and functional groups that can be included in G are one or more alkyl, alkenyl, aryl, amide, thioamide, ester, thioester, ketone (to include oxo-carbons), thioketone, nitrile, nitro, sulfide, sulfoxide, sulfone, disulfide, tertiary amine, ether, urethane, dithiocarbamate, quaternary ammonium and phosphonium, halogen, silyl, silyloxy, and the like, wherein the functional groups requiring substituents are substituted with hydrogen, alkyl, or aryl groups where appropriate;

q is (the valence of G) −1 and can have integral values from 0, when G is a monovalent terminal group, to infinity, when G is a polyvalent linking group, and when linkages are specifically indicated in Formula VI, solid lines represent mandatory linkages and dashed lines represent potential linkages among $X^1$, $Y^1$, $X^2$, $Y^2$, and G.

Michael adducts of Formula VI are synthesized by the Michael reaction of 2-alkenyl azlactone Michael acceptors of Formulae VIIa and VIIb and Michael donors of Formula VIII which are selected from the group consisting of carbon nucleophiles and nitrogen nucleophiles according to Scheme I, below, in which all of the symbols are as previously defined:

Scheme I

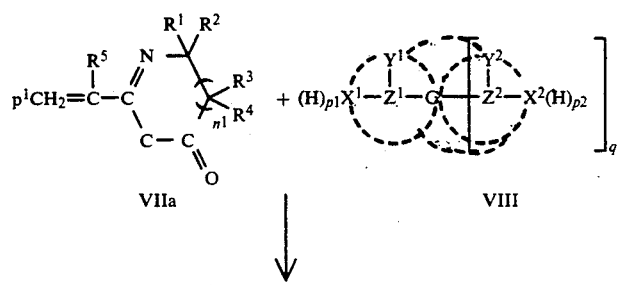

VIIa     VIII

Scheme I

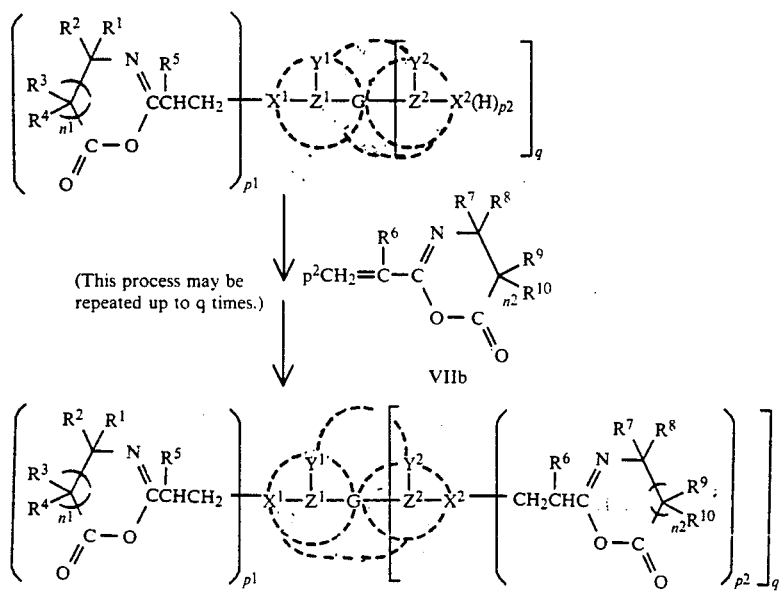

(This process may be repeated up to q times.)

Examples of Michael adducts of Formula VI include those prepared in Examples 1 through 71, below.

Michael acceptors of the invention are 2-alkenyl azlactone compounds represented by Formulae VIIa and VIIb. Examples of suitable 2-alkenyl azlactones include 2-vinyl-4,4-dimethyl-2-oxazolin-5-one [or 2-vinyl-4,4-dimethylazlactone (VDM)], 2-isopropenyl-4,4-dimethyl-2-oxazolin-5-one, 2-vinyl-4-ethyl-4-methyl-2-oxazolin 5-one, 2-vinyl 4,4-dimethyl-1,3-oxazin-6-one, and others disclosed in U.S. Pat. No. 4,305,705 which is incorporated herein by reference. A preferred 2-alkenyl azlactone is VDM (available from SNPE, Inc., Princeton, N.J.).

Carbon nucleophiles useful as Michael donors of the invention are of two kinds: carbon acids and enamines. These two kinds of carbon nucleophiles have often been regarded by organic chemists as being relatively unrelated but that really is not the case. Carbon acidic compounds normally exist in a tautomeric equilibrium of keto and enol forms (see equation below). An added basic catalyst can have a profound influence on the equilibrium, causing a significant shift to the very reactive enolate ion.

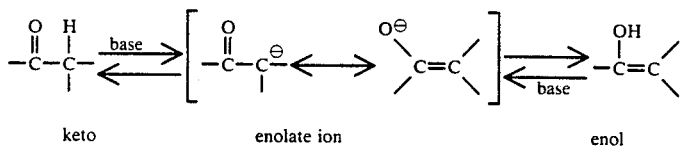

keto        enolate ion        enol

Enol and enolate ion structures are similar to those of enamines and can undergo electrophilic C-alkylation with a 2-alkenyl azlactone Michael acceptor by similar mechanisms as depicted in Scheme II below:

Scheme II

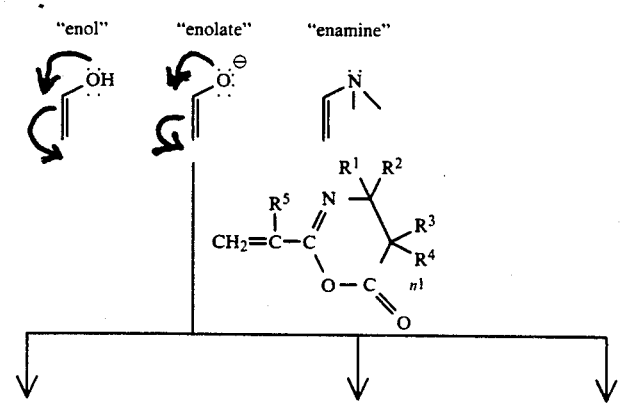

-continued

Scheme II

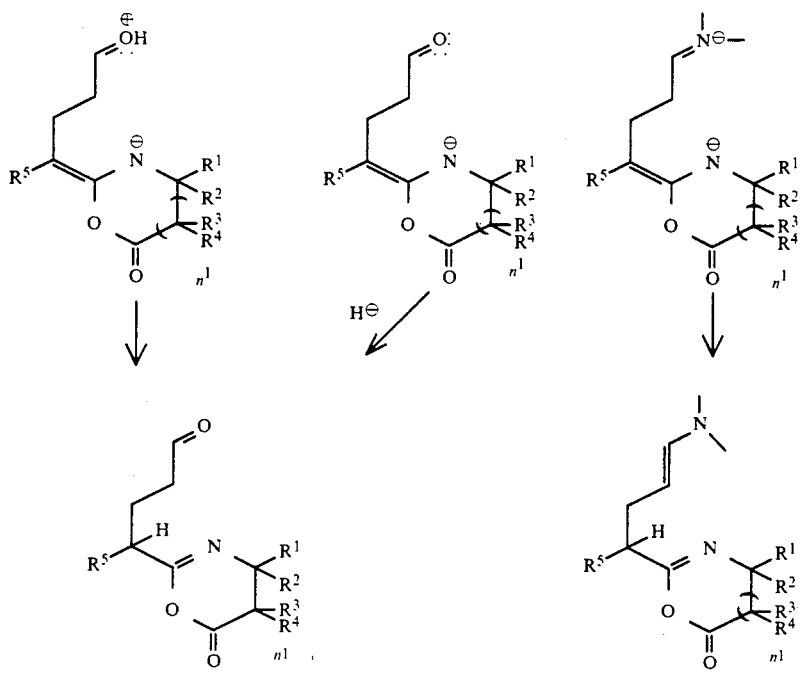

Carbon acids useful in the present invention include those that possess a pKa of less than 15 or are suitably activated by having the carbon acidic function contained within a ring system of six atoms or less and can be represented by Formula VIIIa:

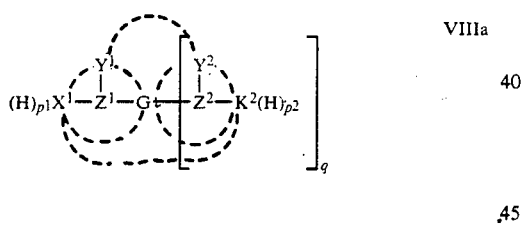

VIIIa wherein $X^1$ and $X^2$ independently can be —$CH_2$; —CH; —C; —$CR_{11}R^{12}$ in which $R^{11}$ and $R^{12}$ are as defined above; —$CHR^{11}$; —$CR^{11}$; —$CW^1W^2$ in which $W^1$ and $W^2$ are as defined above; —$CR^{11}W^1$; —$CHW^1$; and —$CW^1$;

$Z^1$ and $Z^2$ independently can be C, N, or S=O;

$Y^1$ and $Y^2$ independently can be doubly bonded oxygen (=O); doubly bonded sulfur (=S); =$CR^{15}R^{16}$ in which $R^{15}$ and $R^{16}$ are as defined above; and =$NR^{15}$;

G, q, $p^1$, and $p^2$ are as defined above; and when linkages are specifically indicated in Formula VIIIa, solid lines represent mandatory linkages and dashed lines represent potential linkages.

A useful reference for obtaining information regarding the acidities, i.e., pKa's, of organic compounds is "Ionisation Constants of Organic Acids in Aqueous Solution" by E. P. Serjeant and B. Dempsey, IUPAC Chemical Data Series No. 23, Pergamon Press: Oxford, 1979. Formulas of representative useful carbon acidic compounds which possess pKa's of less than 15 or are suitably activated by having the carbon acidic function contained within a ring system of 6 atoms or less include the following:

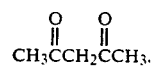

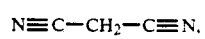

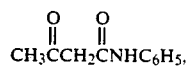

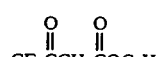

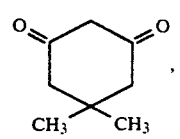

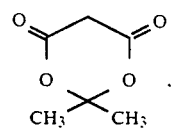

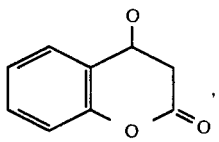

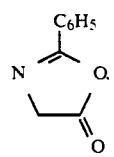

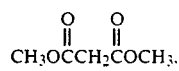

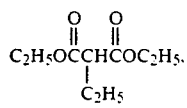

$(CH_3O_2CCH_2)_2SO_2$,

$p-O_2NC_6H_4CH_2C{\equiv}N$,

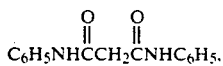

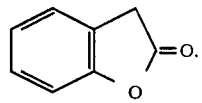

$CH_3NO_2$, $CH_3CH_2NO_2$,

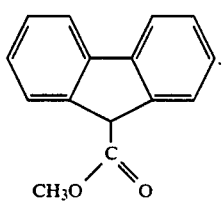

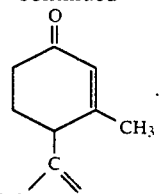

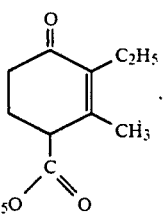

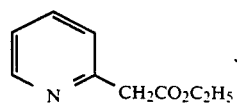

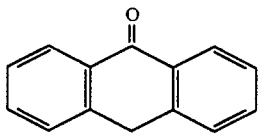

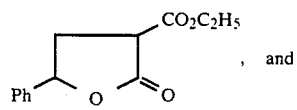

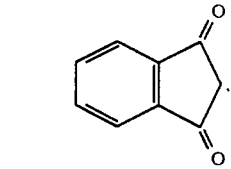, and

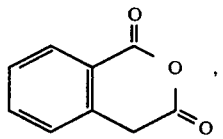

Another series of representative carbon acids useful in the invention include the reaction products of diketene and at least one of amines, alcohols, and mercaptans. Amine reactants can be relatively simple such as mono-, di- and triamines or relatively complex polymeric amines. The preparation of these useful adducts is disclosed in South African Patent 85 2506 and is incorporated herein by reference. Examples of carbon acids prepared in this fashion include the following:

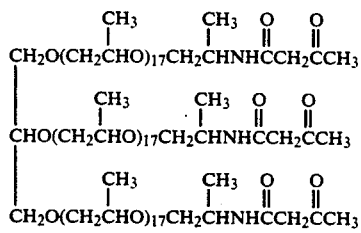

Conditions for effecting the Michael reaction of 2-alkenyl azlactones and the carbon acids of Formula VIIIa vary considerably depending on such factors as the acidity of the carbon acid, the enol content, and associated steric factors that may be operative with a particular carbon acid. Generally, it is advantageous to employ a catalyst, and the most efficient catalysts are bicyclic amidines and trivalent phosphorus compounds described in U.S. Pat. No. 4,874,822 which is incorporated herein by reference. The bicyclic amidines are relatively strong organic bases and may directly catalyze the Michael reaction by forming the reactive enolate ion from the carbon acid. An alternative explanation that may be operative with both kinds of catalysts and especially with the less acidic carbon acids involves initial Michael addition of the catalysts to the 2-alkenyl azlactone. In contrast to the Michael donors of the present invention, these catalysts possess no readily exchangeable proton. Consequently, charged or so-called "zwitterion" structures such as IXa and IXb are formed:

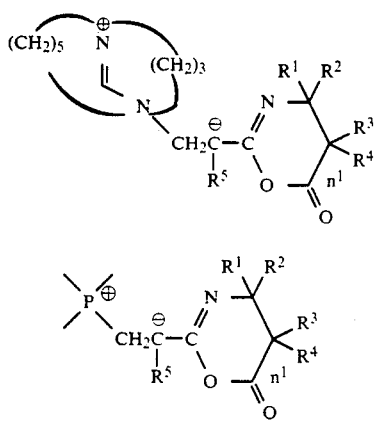

These Michael adducts contain a stabilized carbanion which is a stronger base than either amidine or phosphine catalyst. The zwitterionic intermediate thus formed in situ may be the actual catalytic agent responsible for forming the enolate ion.

Useful bicyclic amidine catalysts include 1,5-diazabicyclo[4.3.0]non-5-ene (DBN), 1,8-diazabicyclo[5.4.0]undec-7-ene (DBU), and 1,5,7-triazabicyclo[4.4.0]dec-5-ene (TBD), and useful trivalent phosphorous compounds include tributylphosphine and trioctylphosphine. DBN, DBU, and tributylphosphine are available from Aldrich Chemical Co. (Milwaukee, WI), and TBD and trioctylphosphine are available from Fluka Chemical Corp. (Ronkonkoma, N.Y.). Effective amounts of the catalysts are from 0.1 to 10.0 mole percent (based on 2-alkenyl azlactone), preferably 1.0 to 7.0 mole percent, and more preferably 2.0 to 5.0 mole percent. While with some of the more acidic and reactive carbon acids Michael reaction proceeds exothermically at room temperature, it is often useful to warm the reaction mixture from 50° C. to 150° C. for periods of up to 72 hours.

Reactions are preferably conducted in the absence of solvent, but if a solvent is required to form a homogeneous reaction solution, the solvent should not react with the reactants or products. Suitable organic solvents include ethyl acetate, methyl ethyl ketone, toluene, chloroform, tetrahydrofuran, N,N-dimethylformamide, N,N-dimethylacetamide, N-methylpyrrolidinone, xylene, decalin, chlorobenzene, and glymes. The amount of solvent employed should be as small as possible because dilution of reactants slows reaction rate. Useful amounts of solvent employed are from 0.9 to 0.1, preferably 0.7 to 0.1, and more preferably 0.5 to 0.1 weight fraction of the reaction solution.

Progress of the Michael reaction can be monitored by observing the disappearance of the carbon-carbon double bond of the 2-alkenyl azlactone Michael acceptor at about 6.25 micrometers (about 1600 cm$^{-1}$) in the infrared spectrum. Alternatively, among other useful interpretive resonances, the appearance of resonances in the $^1$H-NMR spectrum for the $-X^1-CH_2-CHR^5-$ portion of the Michael adducts of Formula VI serves as both an excellent qualitative and quantitative marker for the progress of the Michael reaction. The positions of these resonances are highly variable, however, depending on factors such as the nature of $X^1$, $R^5$, and other groups present in the compound; of the prepared examples vide infra of Michael adducts derived from Michael donors of Formula VIIIa these resonances were observed in the region from about $\delta$1.6 to 3.0 ppm.

Enamine compounds of the invention are represented by Formula VIIIb:

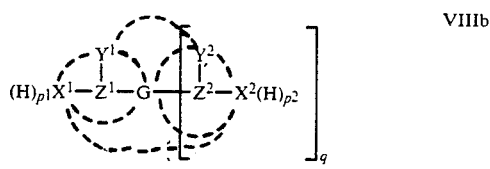

wherein $X^1$ and $X^2$ independently can be $-C$, $-CH$, $-CR^{11}$ in which $R^{11}$ is as defined above, and $-CHR^{11}$;

$Z^1$ and $Z^2$ are C;

$Y^1$ and $Y^2$ independently can be $-CR^{15}=CR^{16}R^{17}$ and $-NR^{18}R^{19}$ in which $R^{15}$, $R^{16}$, $R^{17}$, $R^{18}$, and $R^{19}$ are as defined above;

G, q, $p^1$, and $p^2$ are as defined above; and when linkages are specifically indicated in Formula VIIIb, solid lines represent mandatory linkages and dashed lines represent potential linkages.

Formulas of useful enamine compounds include:

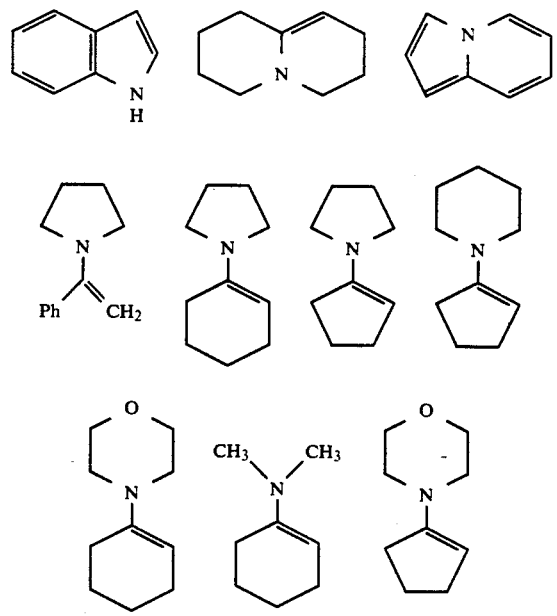

-continued

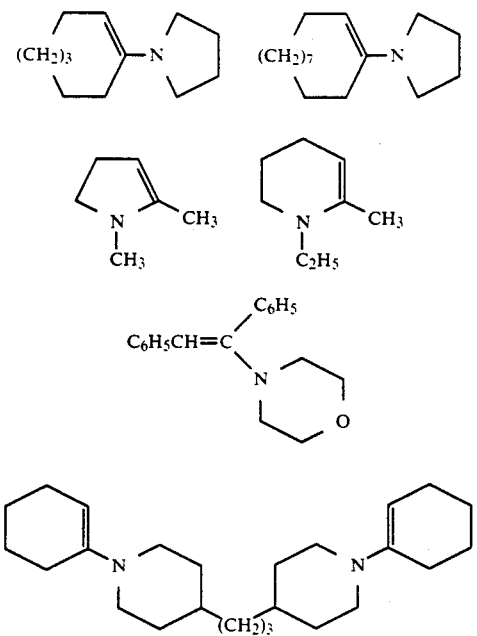

Pyrrole is also useful and reacts in the 2-position as a conjugated enamine.

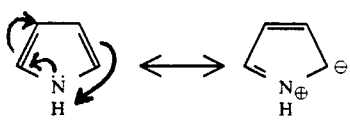

Michael reaction of the enamines of Formula VIIIb with 2-alkenyl azlactones generally requires no added catalyst but may require employment of heating conditions specified with carbon acid Michael donors of Formula VIIIa. Infrared and $^1$H-NMR spectroscopy are again useful in monitoring the course of the reaction. With donor compounds of Formula VIIIb, —X$^1$C-H$_2$—CHR$^5$— resonances of prepared examples were observed in the δ2.4 to 3.2 ppm region of the $^1$H-NMR spectrum.

As with the carbon nucleophiles, the nitrogen nucleophiles useful in the invention are of two kinds: imidic compounds and selected nitrogen heterocycles. The nucleophilic nitrogens of these compounds possess a hydrogen and two groups which are not hydrogen. Unlike the secondary amines employed to prepare Michael reaction products of U.S. Pat. Nos. 4,639,286 and 4,485,236, the nitrogen nucleophiles of the present invention possess at least one electron withdrawing group on nitrogen. Because of this, the relative nucleophilicities of the instant nitrogen nucleophiles are significantly lower than the secondary amines of U.S. Pat. Nos. 4,485,236 and 4,639,286, such that catalysts generally are required for the Michael reaction to occur. An approximation (at least to the first order) of the nucleophilicity of a nitrogen compound is indicated by the compound's basicity, with relatively high conjugate acid pKa's indicating high nucleophilicities. With the relatively highly nucleophilic secondary amines which required no catalyst to effect the Michael reaction disclosed in U.S. Pat. Nos. 4,639,286 and 4,485,236 useful secondary amines generally were those whose conjugate acids possessed pKa's greater than about 5. Due to the influence of the electron withdrawing group(s) the conjugate acids of nitrogen nucleophiles useful in the present invention generally possess pKa's of 5 or less. Therefore, the present nitrogen nucleophiles differ from the art compositionally, in terms of their nucleophilicity, and generally in their method of preparation.

The imidic Michael donors compounds of the present invention are indicated by Formula VIIIc:

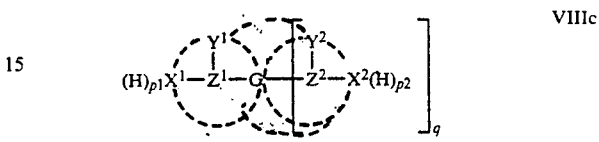

wherein

X$^1$ and X$^2$ independently can be —NW$^1$ in which W$^1$ is as defined above;

Z$^1$ and Z$^2$ independently can be C or S=O;

Y$^1$ and Y$^2$ independently can be doubly bonded oxygen (=O); doubly bonded sulfur (=S); =NR$^{15}$ in which R$^{15}$ is as defined above;

G, q, p$^1$, and p$^2$ are as defined above; and when linkages are specifically indicated in Formula VIIIc, solid lines represent mandatory linkages and dashed lines represent potential linkages.

Formulas of useful imidic compounds include:

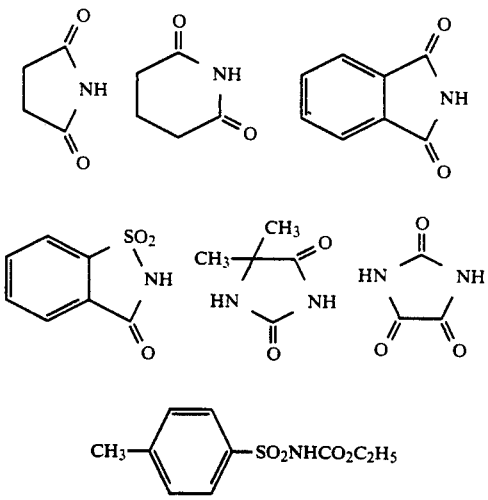

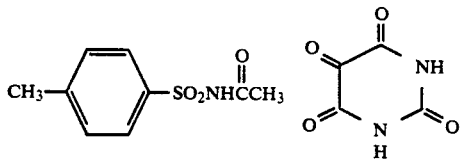

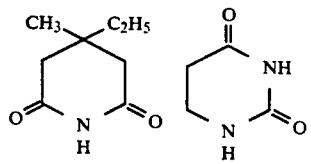

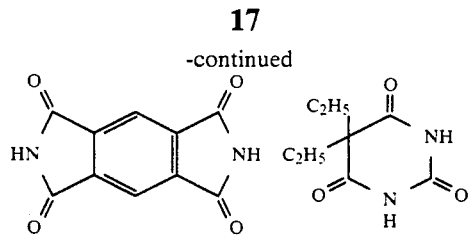

Michael reactions of 2-alkenyl azlactones and the Michael donors of Formula VIIIc generally require catalysts. The most effective catalysts in our hands have been the bicyclic amidine and trivalent phosphorous compounds previously indicated with the Formula VIIIa compounds. Aforementioned heating conditions, reaction times, and solvents are appropriate with these reactants as well. Relevant —$X^1CH_2CHR^5$— resonances have been observed between $\delta 2.7$ and 4.2 ppm in the $^1$H-NMR spectra Selected nitrogen heterocycle Michael donors of the invention are those indicated by Formula VIIId:

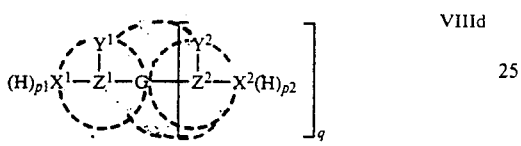

VIIId wherein $X^1$ and $X^2$ independently can be —$NR^{14}$ in which $R^{14}$ is as defined above;

$Z^1$ and $Z^2$ independently can be C, N, or S=O;

$Y^1$ and $Y^2$ independently can be doubly bonded oxygen (=O); doubly bonded sulfur (=S); =$CR^{15}R^{16}$ in which $R^{15}$ and $R^{16}$ are as defined above; or =$NR^{15}$;

G, q, $p^1$, and $p^2$ are as defined above; and when linkages are specifically indicated in Formula VIIId, solid lines represent mandatory linkages and dashed lines represent potential linkages.

Formulas of useful nitrogen heterocycles include:

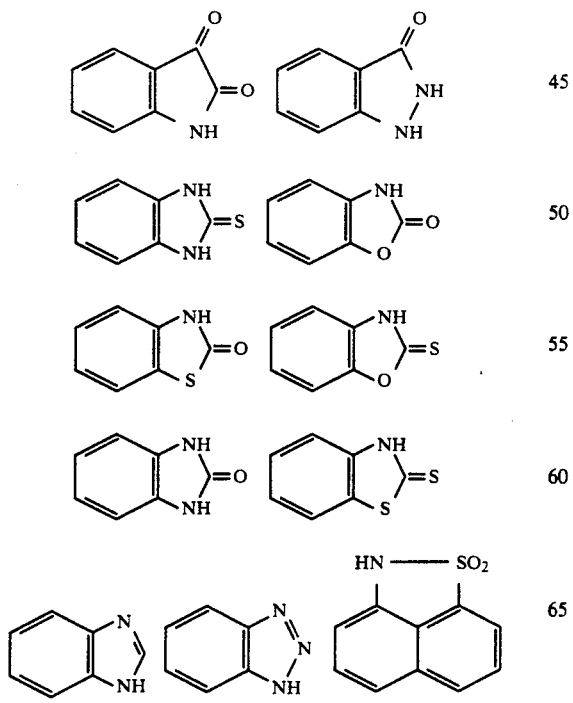

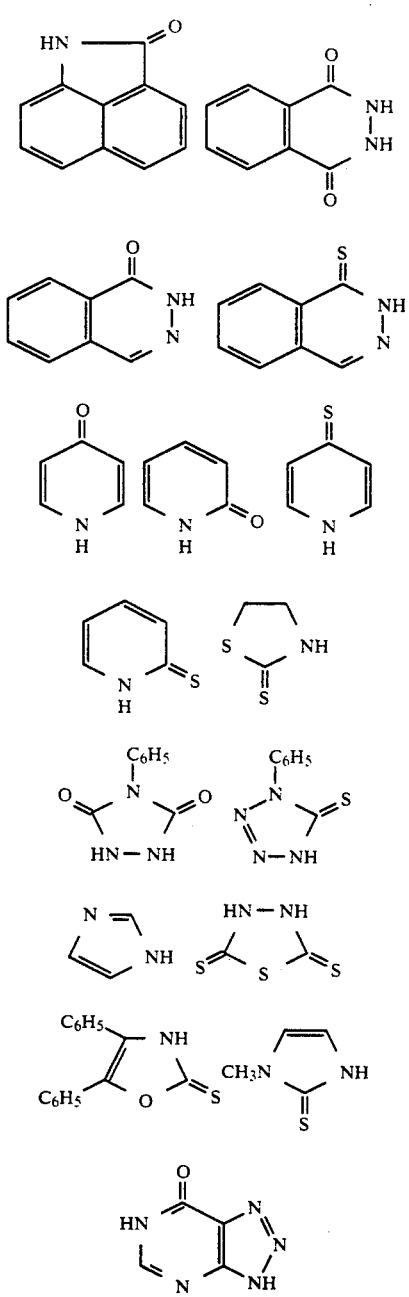

As with the other Michael donors, Michael reactions of 2-alkenyl azlactones and the nitrogen heterocycles of Formula VIIId are most efficiently conducted in the presence of bicyclic amidine and trivalent phosphine catalysts employing similar reaction conditions. The $X^1$—$CH_2$—$CHR^5$— resonances of these Michael adducts have been observed in the $^1$H-NMR spectra over the region from $\delta 2.3$ to 5.2 ppm.

As is apparent to one skilled in the art, a number of compounds exist which contain a plurality of Michael donor groups comprising at least two carbon acids, enamines, imides, and nitrogen heterocycles and are useful in the invention. Formulas of some of these compounds are listed below:

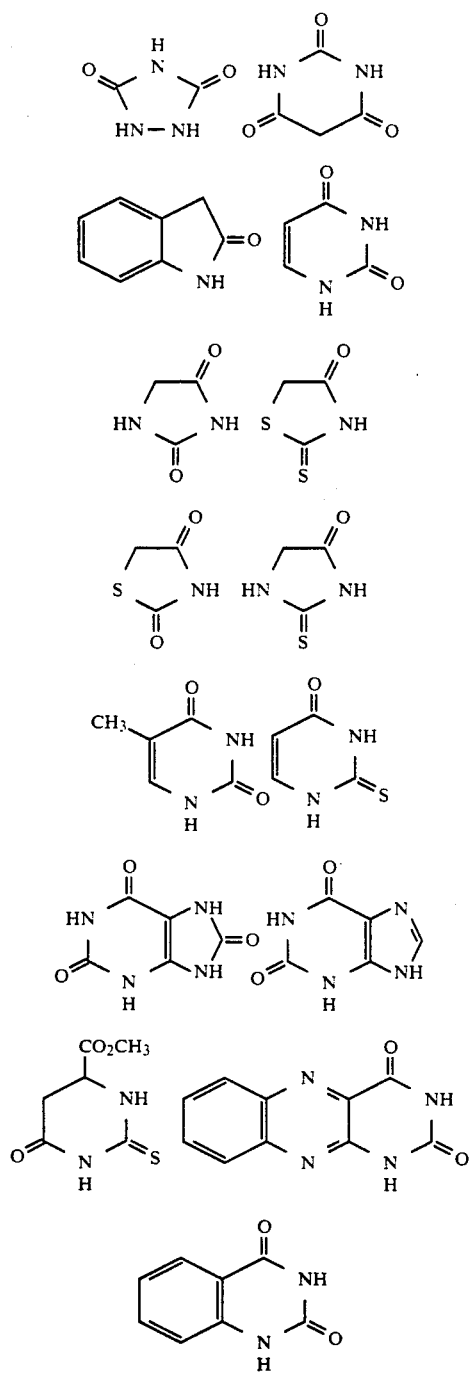

The utility of the various azlactone Michael adducts of Formula VI is considerable. The adducts which contain a plurality of azlactone groups (multi-azlactones) are useful as step growth monomers and crosslinking agents in a variety of constructions including adhesives, sealants, and coatings. A distinct advantage in the employment of these multi-azlactones is that special comonomers for the step growth polymerization are not required. Ordinary and inexpensive polyols and polyamines function very effectively as comonomers. It is also contemplated that compounds of Formula VI which contain only one azlactone group are useful. The structurally diverse monoazlactone-functional materials that were synthesized illustrate the rich variety of the novel chemistry disclosed herein. In addition, it is envisioned that the 2-alkenyl azlactones can perform a coupling or linking function between a Michael donor that has some intrinsically useful property to a polymer (or even another relatively small molecule) that contains groups, pendant or at the termini of the main-chain, capable of reacting with an azlactone. The monoazlactone-functional adducts of Formula VI represent an intermediate, reactive material which can then be reacted with an amino- or hydroxy-functional polymer or other molecule to accomplish covalent attachment of the Michael donor with its attending desirable, modifying property.

Objects and advantages of this invention are further illustrated by the following examples, but the particular materials and amounts thereof recited in these examples, as well as other conditions and details, should not be construed to unduly limit the invention. In the examples, the $^1$H-NMR resonances recorded in the various tables were obtained either in deuteriochloroform or hexadeuterodimethyl sulfoxide solution, and the chemical shifts were reported relative to the tetramethylsilane resonance at $\delta 0$ ppm. When the $CH_2$ and $CHR^5$ resonances were sufficiently different, the approximate centers of the two multiplets were recorded and separated by a comma. Otherwise the range of the broad multiplet resonances were reported and separated by a dash. Resonances were reported to the nearest 0.1 ppm. Also in the tables, superscripts A, B, C, and D mean that DBU, trioctylphosphine, trifluoroacetic acid, and no catalyst, respectively, were utilized to conduct the reactions. Symbols utilized in this application include Ph for phenyl, Et for ethyl, Me for methyl, sb means single bond, and ep means electron pair. In certain cases Michael addition was accompanied by ring-opening of the azlactone, E indicates that the H-NMR spectrum was complicated and values in parentheses indicate the ratio of Michael:ring-opened products. VDM means 2-vinyl-4,4-dimethylazlactone (in which $R^1$ and $R^2$=methyl, $R^3$ and $R^4$ do not exist since $n^1$=O, and $R^5$=hydrogen); VEM means 2-vinyl-4-ethyl-4-methylazlactone synthesized by the method of Heilmann, et al., *J. Polym. Sci.: Polym. Chem. Ed.*, 22, 1179 (1984) (in which $R^1$=ethyl and $R^2$=methyl, $R^3$ and $R^4$ do not exist since $n^1$=O, and $R^5$=hydrogen); IDM means 2-isopropenyl-4,4-dimethylazlactone synthesized by the method of Taylor, et al., *J. Polym. Sci. Polym. Lett.*, 9, 187 (1971) (in which $R^1$, $R^2$, and $R^5$ are methyl and $R^3$ and $R^5$ do not exist since $n^1$=O); and VOX means 2-vinyl-4,4-dimethyl-2-oxazin-6-one synthesized by the method of Heilmann, et al., supra, (in which $R^1$ and $R^2$ are methyl, $R^3$ and $R^4$ are hydrogen and $n^1$=1, and $R^5$ is hydrogen).

EXAMPLE 1

This example teaches the synthesis of an azlactone-functional Michael adduct of Formula VI by reaction of a 2-alkenyl azlactone with a carbon acid Michael donor of Formula VIIIa.

Dimethyl malonate (79.20 grams; 0.60 mole), VDM (166.80 grams; 1.20 moles), and DBU (3.65 grams; 2 mole percent based on VDM) were mixed without incident in a sealed reaction vessel; the reaction solution was then placed in an oven at 70° C. After 36 h the $^1$H-NMR spectrum revealed (based on the integration of the newly formed —$CH_2CH_2$— resonances at $\delta 2.3$ and 2.5 ppm compared to vinyl protons of the VDM reagent at $\delta 5.9$ and 6.3 ppm) that approximately 70% conversion to the Michael addition product had been achieved. Another 3.65 grams of DBU were added and additional heating at 70° C. for 24 h provided a reaction product whose $^1$H-NMR spectrum contained no vinyl proton resonances. The structure of the bis(azlactone) adduct was confirmed by IR, $^1$H-NMR, and $^{13}$C-NMR spectroscopy. The colorless, viscous fluid product slowly crystallized to a white solid melting at 73°–74° C.

A similar result was obtained using trioctylphosphine (TOP) (5 mole percent) as a catalyst instead of DBU.

EXAMPLES 2-22

Employing the procedure of Example 1, the following azlactone Michael adducts of Formula VI were prepared. In Table I are contained some of the relatively simple compounds of Formula VI that illustrate the invention in which $q=0$ and no bonds exist among $X^1$, G, and $Y^1$.

TABLE I

| Ex. | Michael Donor Formula VIIIa | 2-Alkenyl Azlactone Formula VIIa | $p^1$ | $X^1$ | $Z^1$ | $Y^1$ | G | $X^1CH_2CHR^5$ Shifts |
|---|---|---|---|---|---|---|---|---|
| 2 | $CH_3CCH_2CCH_3$ (O,O) | VDM$^B$ | 2 | $CW^1$<br>$W^1 = COCH_3$ | C | =O | $CH_3$ | 2.2, 2.3 |
| 3 | $CH_3NO_2$ | VDM$^B$ | 3 | C | N | =O | =O | 2.4, 2.6 |
| 4 | $NCCH_2CN$ | VDM$^B$ | 2 | $CW^1$<br>$W^1 = CN$ | C | $=NR^{15}$<br>$R^{15} = ep$ | sb to $Y^1$ | 2.5, 2.9 |
| 5 | $EtO_2CCH_2CPh$ (O) | VDM$^B$ | 2 | $CW^1$<br>$W^1 = COPh$ | C | =O | OEt | 2.3–2.7 |
| 6 | $PhCCH_2CPh$ (O,O) | VDM$^B$ | 2 | $CW^1$<br>$W^1 = COPh$ | C | =O | Ph | 2.5, 2.7 |
| 7 | $CF_3CCH_2CCH_3$ (O,O) | VDM$^D$ | 2 | $CW^1$<br>$W^1 = COCH_3$ | C | =O | $CF_3$ | 2.2–2.7 |
| 8 | $C_2H_5NO_2$ | VDM$^B$ | 2 | $CR^{11}$<br>$R^{11} = CH_3$ | N | =O | =O | 2.3, 2.5 |
| 9 | $PhNHCCH_2CCH_3$ (O,O) | VDM$^B$ | 2 | $CW^1$<br>$W^1 = COCH_3$ | C | =O | NHPh | 2.4–2.5 |
| 10 | $(EtO_2C)_2CHEt$ | VDM$^B$ | 1 | $CR^{11}W^1$<br>$R^{11} = Et$<br>$W^1 = CO_2Et$ | C | =O | OEt | 2.3, 2.5 |
| 11 | $O_2N-C_6H_4-CH_2CN$ | VDM$^B$ | 2 | $CW^1$<br>$W^1 = R^{11}R^{12}C=CR^{13}$<br>$R^{11} = H, R^{12} =$<br>$-CH=C(NO_2)-$<br>$R^{13} = -CH=CH-$ | C | $=NR^{15}$<br>$R^{15} = ep$ | sb to $Y^1$ | 2.4, 2.6 |
| 12 | $CF_3CCH_2CO_2Et$ (O) | VDM$^B$ | 2 | $CW^1$<br>$W^1 = COCF_3$ | C | =O | OEt | 2.3, 2.5 |
| 13 | $CF_3CCH_2CCF_3$ (O,O) | VDM$^D$ | 2 | $CW^1$<br>$W^1 = COCF_3$ | C | =O | $CF_3$ | 2.5, 2.7 |
| 14 | $CF_3SCH_2SCF_3$ (O,O,O,O) | VDM$^D$ | 2 | $CW^1$<br>$W^1 = SO_2CF_3$ | $\overset{O}{\underset{S}{\|}}$ | =O | $CF_3$ | 2.9, 3.0 |
| 15 | $CH_3SCH_2CPh$ (O,O) | VDM$^B$ | 2 | $CW^1$<br>$W^1 = COPh$ | $\overset{O}{\underset{S}{\|}}$ | =O | $CH_3$ | 2.5–2.7 |
| 16 | pyridyl-$CH_2CO_2Et$ | VDM$^B$ | 2 | $CW^1$<br>$W^1 = R^{11}N=(R^{12})C-$<br>$R^{11} = R^{12} =$<br>$-CH=CH-$ | C | =O | OEt | 2.4, 2.5 |
| 17 | $PhNHCCH_2CNHPh$ (O,O) | VDM$^B$ | 2 | $CW^1$<br>$W^1 = CONHPh$ | C | =O | NHPh | 2.3, 2.5 |

TABLE I-continued

| Ex. | Michael Donor Formula VIIIa | 2-Alkenyl Azlactone Formula VIIa | $p^1$ | $X^1$ | $Z^1$ | $Y^1$ | G | $X^1CH_2CHR^5$ Shifts |
|---|---|---|---|---|---|---|---|---|
| 18 | $CH_3SCH_2S$(—$C_6H_4$—)$CH_3$ with $SO_2$ groups | VDM$^A$ | 2 | $CW^1$ $W^1$ = SO CH | O=S | =O | $H_3CC_6H_4$ | 2.7, 2.9 |
| 19 | $EtO_2CCH_2CO_2Et$ | IDM$^A$ | 2 | $CW^1$ $W^1$ = $CO_2Et$ | C | =O | OEt | 2.3, 2.5 |
| 20 | $EtO_2CCH_2CO_2Et$ | VOX$^A$ | 2 | $CW^1$ $W^1$ = $CO_2Et$ | C | =O | OEt | E(60:40) |
| 21 | $MeO_2CCH_2CO_2Me$ | VEM$^B$ | 2 | $CW^1$ $W^1$ = $CO_2Me$ | C | =O | OMe | 2.3, 2.6 |
| 22 | $MeO_2CCH_2CO_2Me$ | VEM$^B$ | 1 | $CHW^1$ $W^1$ = $CO_2Me$ | C | =O | OMe | 2.3, 2.6 |

EXAMPLES 23–27

The following examples were conducted employing the procedure of Example 1 with carbon acids of Formula VIIIa that are slightly more complex. In the resulting Michael adducts of Formula VI (see TABLE II below), q is still 0, but bonding exists among $X^1$, $Y^1$, and G.

EXAMPLES 28–31

The following examples were conducted with carbon acidic Michael donors of Formula VIIIa in which q is not equal to zero. The resulting Formula VI Michael adducts (See TABLE III below) were prepared using VDM as the Michael acceptor by the method of Example 1.

TABLE II

| Ex. | Michael Donor Formula VIIIa | 2-Alkenyl Azlactone Formula VIIa | $p^1$ | $X^1$ | $Z^1$ | $Y^1$ | G | $X^1CH_2CHR^5$ Shifts |
|---|---|---|---|---|---|---|---|---|
| 23 | chroman-2,4-dione | VDM$^B$ | 2 | $CW^1$ $W^1$ = $CO_2R^{11}$ $R^{11}$ = sb to G | C | =O | o-$C_6H_4$ | 2.4, 2.5 |
| 24 | indane-1,3-dione | VDM$^D$ | 2 | $CW^1$ $W^1$ = $COR^{11}$ $R^{11}$ = sb to G | C | =O | o-$C_6H_4$ | 2.3, 2.4 |
| 25 | 5,5-dimethyl-1,3-cyclohexanedione | VDM$^D$ | 2 | $CW^1$ $W^1$ = $COR^{11}$ $R^{11}$ = sb to G | C | =O | $CH_2$—MeCMe—$CH_2$— | 2.4, 2.7 |
| 26 | 2,2-dimethyl-1,3-dioxane-4,6-dione | VDM$^B$ | 2 | $CW^1$ $W^1$ = $CO_2R^{11}$ $R^{11}$ = —C(CH$_3$)$_2$— | C | =O | —O— | 2.5, 2.6 |
| 27 | anthrone | VDM$^B$ | 2 | $CR^{11}$ $R^{11}$ = —$C_6H_4C$(=O)— | C | =$CR^{15}R^{16}$ $R^{15}$ = —CH=CH— $R^{16}$ = sb to $R^{11}$ | —CH=CH— | 1.7, 2.7 |

TABLE III

| Ex. | Michael Donor Formula VIIIa | q | $p^1$ | $X^1$ | $Z^1$ | $Y^1$ | G | $Y^2$ | $Z^2$ | $X^2$ | $p^2$ | Methylene Shifts |
|---|---|---|---|---|---|---|---|---|---|---|---|---|
| 28$^B$ | $(MeO_2CCH_2)_2SO_2$ | 1 | 2 | $CW^1$ $W^1$ = $CO_2Me$ | | | [—$SO_2$—] | | | $CW^2$ $W^2$ = $CO_2Me$ | 2 | 2.3–2.9 |

TABLE III-continued

| Ex. | Michael Donor Formula VIIIa | q | $p^1$ | $X^1$ | $Z^1$ | $Y^1$ | Azlactone Michael Adduct G | $Y^2$ | $Z^2$ | $X^2$ | $p^2$ | Methylene Shifts |
|---|---|---|---|---|---|---|---|---|---|---|---|---|
| 29[B] | (indanone structure) | 1 | 2 | $CR^{11}$ $R^{11}$ = o-$C_6H_4$ | | | [—C—] ‖ O | | | $CR^{11}$ $R^{11}$ = sb to $X^1$ | 2 | 2.2–2.4 |
| 30[B] | Glycerol[(OCH$_2$CH)$_{17}$— —NHCCH$_2$CCH$_3$]$_3$ ‖ ‖ O O with CH$_3$ | 2 | 2 | $CW^1$ $W^1$ = COMe | C | =O | Glycerol[(OCH$_2$CH)$_{17}$— —NH—]$_3$ with CH$_3$ | =O | C | $CW^2$ $W^2$ = COMe | 2 | 2.3, 2.4 |
| 31[B] | EtC[CH$_2$(OCH$_2$CH)$_2$— —NHCCH$_2$CCH$_3$]$_3$ ‖ ‖ O O with CH$_3$ | 2 | 2 | $CW^1$ $W^1$ = COMe | C | =O | EtC[CH$_2$(OCH$_2$CH)$_2$— —NH—]$_3$ with CH$_3$ | =O | C | $CW^2$ $W^2$ = COMe | 2 | 2.3, 2.4 |

EXAMPLE 32

This example teaches the Michael reaction of enamine compounds of Formula VIIIb and 2-alkenyl azlactones.

VDM (19.46 grams; 0.14 mole) and 1-pyrrolidino-1-cyclopentene (available from Aldrich Chemical Co., Milwaukee, Wis.) (9.59 grams; 0.07 mole) were combined, causing a warming of the reaction mixture to ca. 60° C. and a concomitant increase in viscosity. After heating at 70° C. for 16 h, $^1$H-NMR indicated quantitative conversion to the bis(Michael adduct) with newly formed methylene resonances in the δ2.3–2.8 ppm region. The resulting Michael adduct of Formula VI possessed $p^1=p^2=q=1$, $X^1=CR^{11}$ ($R^{11}=(CH_2)_2$), $Z^1$, $Y^1$, G, $Y^2$, $Z^2$ taken together form =C(—NC$_4$H$_8$)—, $X^2=CR^{11}$ ($R^{11}=$sb to $X^1$).

EXAMPLES 33–36

The following examples were conducted with enamine Michael donors of Formula VIIIb. The resulting Formula VI Michael adducts were prepared using VDM as the Michael acceptor by the method of Example 32. The data is given in TABLE IV, below.

TABLE IV

| Ex. | Michael Donor Formula VIIIa | q | $p^1$ | $X^1$ | $Z^1$ | $Y^1$ | Azlactone Michael Adduct G | $Y^2$ | $Z^2$ | $X^2$ | $p^2$ | $CH_2CHR^5$ Shifts | $CH_2CHR^6$ Shifts |
|---|---|---|---|---|---|---|---|---|---|---|---|---|---|
| 33[D] | (1-pyrrolidino-cyclohexene) | 1 | 1 | $CR^{11}$ $R^{11}$ = —(CH$_2$)$_3$— | | | [=C—N⟨⟩] | | | $CHR^{11}$ $R^{11}$ = sb | 1 | 2.3–2.7 | 2.3–2.7 |
| 34[D] | (1-morpholino-cyclohexene) | 1 | 1 | $CR^{11}$ $R^{11}$ = —(CH$_2$)$_3$— | | | [=C—N⟨⟩O] | | | $CHR^{11}$ $R^{11}$ = sb | 1 | 2.4–2.7 | 2.4–2.7 |
| 35[D] | (indole) | 0 | 1 | $CR^{11}$ $R^{11}$ = o-$C_6H_4$ | C | $NR^{18}R^{19}$ $R^{18}$ = H $R^{19}$ = sb to $X^1$ | H | NA | NA | NA | NA | 2.8, 3.2 | NA |
| 36[D] | (pyrrole) | 1 | 1 | $CR^{11}$ $R^{11}$ = NH | | | [=CH—CH=] | | | $CR^{11}$ $R^{11}$ = sb to $X^1$ | 1 | 2.7, 2.9 | 2.8, 3.0 |

EXAMPLE 37

This example teaches the Michael reaction of imidic compounds of Formula VIIIc and 2-alkenyl azlactones.

Trioctylphosphine (0.19 gram; 5 mole percent based on VDM) was added to a solution containing succinimide (0.99 gram; 0.01 mole), VDM (1.39; 0.01 mole), and dimethylacetamide (2.38 grams; solvent weight fraction =0.50) without incident. Heating at 65° C. for 3.5 h produced the Michael adduct exhibiting newly formed H-NMR methylene resonances at δ2.7 and 3.9 ppm.

A similar result was obtained by heating a slurry of succinimide, VDM, and DBU (5 mole percent) to 125° C. for 10 minutes.

EXAMPLES 38–42

The procedure of Example 37 was adopted for the following examples in which $n^1=q=0$, $p^1=1$, and $X^1=NW^1$. The data is given in TABLE V, below.

TABLE V

| Ex. | Michael Donor Formula VIIIc | 2-Alkenyl Azlactone Formula VIIa | Azlactone Michael Adduct $W^1$ | $Z^1$ | $Y^1$ | G | $X^1$CHCHR$^5$ Shifts |
|---|---|---|---|---|---|---|---|
| 38[B] | (phthalimide structure) | VDM | COR$^{11}$ R$^{11}$ = sb to G | C | =O | o-C$_6$H$_4$ | 3.0, 3.8 |
| 39[B] | (benzisothiazole dioxide structure) | VDM | SO$_2$R$^{11}$ R$^{11}$ = sb to G | C | =O | o-C$_6$H$_4$ | 3.0, 4.2 |
| 40[B] | CH$_3$—(C$_6$H$_4$)—SO$_2$NHCO$_2$Et | VDM | CO$_2$R$^{11}$ R$^{11}$ = Et | S∥O | =O | CH$_3$C$_6$H$_4$ | 3.0, 4.2 |
| 41[B] | CH$_3$—(C$_6$H$_4$)—SO$_2$NHC(O)CH$_3$ | VDM | COR$^{11}$ R$^{11}$ = Me | S∥O | =O | CH$_3$C$_6$H$_4$ | 2.9, 4.1 |
| 42[A] | PhN=N—(C$_6$H$_4$)—OC(O)NHSO$_2$—(C$_6$H$_4$)—CH$_3$ | VDM | CO$_2$R$^{11}$ R$^{11}$ = C$_6$H$_4$=NPh | O∥S | =O | MeC$_6$H$_4$ | 3.1, 4.4 |
| 43[A] | (succinimide structure) | IDM | COR$^{11}$ R$^{11}$ = sb to G | C | =O | —CH$_2$CH$_2$— | 3.0, 3.8 |

EXAMPLE 44

The procedure of Example 37 was again utilized for the reaction of the diimide parabanic acid with VDM to provide the Michael adduct wherein $q=p^1=p^2=1$, $X^1=X^2=NW^1$ ($W^1=COR^{11}$ and $R^{11}=sb$), and $Z^1$, $Y^1$, G, $Y^2$, $Z_2$ together form a single carbonyl. The methylene resonances appeared at $\delta 2.8$ and 3.8 ppm in the $^1$H-NMR spectrum.

EXAMPLE 45

This example teaches the Michael reaction of 2-alkenyl azlactones and nitrogen heterocyles of Formula VIIId.

VDM (13.9 grams; 0.10 mole) was cooled to 0° C. and mixed with 1-phenyl-1H-tetrazole-5-thiol (available from Aldrich Chemical Co., Milwaukee, Wis.) (17.8 grams; 0.10 mole). The mixture was allowed to warm to room temperature and maintained at this temperature overnight. $^1$H-NMR of the product in DMSO-d$_6$ showed resonances for the methylene groups at 3.6 and 3.1 ppm, indicative of the S-alkylated Michael addition product. When this material was heated at 100° C. overnight, the 4-N-alkylated product was formed as evidenced by the methylene resonances at $\delta 4.7$ and 3.2 ppm. The 4-N-alkylated Michael adduct [Formula VI in which $^1=1$, $X^1=NR^{14}$ (wherein $R^{14}$ = —N=N—N(Ph) and G is a single bond to $X^1$), $Z^1=C$, $Y^1=(=S)$, and $q=0$] could also be prepared by heating an equimolar mixture of the reactants at 100° C. overnight.

EXAMPLES 46–63

Examples 46–64 were conducted in the manner of Example 45 and illustrate the rich variety of structural features of Michael donors of Formula VIIId of the invention in which $q=0$ and $p^1=1$ in TABLE VI, below.

TABLE VI

| Ex. | Michael Donor Formula VIIId | 2-Alkenyl Azlactone Formula VIIa | Azlactone Michael Adduct $X^1$ | $Z^1$ | $Y^1$ | G | $X^1$CH$_2$CHR$^5$ Shifts |
|---|---|---|---|---|---|---|---|
| 46 | (1-phenyl-tetrazole-5-thione structure) | IDM[C] | NR$^{14}$ R$^{14}$ = —N=N—N(Ph) | C | =S | sb to $X^1$ | 3.4, 4.6 |

TABLE VI-continued

| Ex. | Michael Donor Formula VIIId | 2-Alkenyl Azlactone Formula VIIa | Azlactone Michael Adduct $X^1$ | $Z^1$ | $Y^1$ | G | $X^1CH_2CHR^5$ Shifts |
|---|---|---|---|---|---|---|---|
| 47 | benzotriazole | $IDM^C$ | $NR^{14}$<br>$R^{14} = o\text{-}C_6H_4$ | N | $=NR^{15}$<br>$R^{15} =$ sb to $X^1$ | ep | 3.5, 5.1 |
| 48 | 2-thiopyridone | $VDM^D$ | $NR^{14}$<br>$R^{14} = -CH=CH-$ | C | $=S$ | $-CH=CH-$ | 3.2, 4.9 |
| 49 | 2-pyridone | $VDM^B$ | $NR^{14}$<br>$R^{14} = -CH=CH-$ | C | $=O$ | $-CH=CH-$ | 3.0, 4.4 |
| 50 | 4-pyridone | $VDM^B$ | $NR^{14}$<br>$R^{14} = -CH=CH-$ | C | $=CR^{15}R^{16}$<br>$R^{15} = H$<br>$R^{16} = -\overset{\overset{\displaystyle O}{\|}}{C}-$ | H | 2.5, 4.0 |
| 51 | 1-methyl-2-thioimidazoline | $VDM^B$ | $NR^{14}$<br>$R^{14} = -CH=CH-$ | C | $=S$ | $-N(Me)-$ | 3.0, 4.4 |
| 52 | cyclic thiocarbamate | $VDM^B$ | $NR^{14}$<br>$R^{14} = -CH_2CH_2-$ | C | $=S$ | $-S-$ | 3.3, 4.2 |
| 53 | naphthosultam | $VDM^B$ | $NR^{14}$<br>$R^{14} =$ naphthyl | O<br>S | $=O$ | sb to $X^1$ | 3.1, 4.3 |
| 54 | naphtholactam | $VDM^B$ | $NR^{14}$<br>$R^{14} =$ naphthyl | C | $=O$ | sb to $X^1$ | 3.0, 4.3 |
| 55 | 2-mercaptobenzothiazole | $VDM^A$ | $NR^{14}$<br>$R^{14} = o\text{-}C_6H_4$ | C | $=S$ | $-S-$ | 3.0, 4.8 |
| 56 | 2-hydroxybenzothiazole | $VDM^D$ | $NR^{14}$<br>$R^{14} = o\text{-}C_6H_4$ | C | $=O$ | $-S-$ | 2.9, 4.3 |

TABLE VI-continued

| Ex. | Michael Donor Formula VIIId | 2-Alkenyl Azlactone Formula VIIa | Azlactone Michael Adduct | | | | $X^1CH_2CHR^5$ Shifts |
|---|---|---|---|---|---|---|---|
| | | | $X^1$ | $Z^1$ | $Y^1$ | G | |
| 57 | 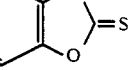 | VDM$^D$ | $NR^{14}$<br>$R^{14} = $ o-C$_6$H$_4$ | C | =S | —O— | 3.1, 4.6 |
| 58 | 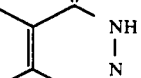 | VDM$^d$ | $NR^{14}$<br>$R^{14} = $ —N=CH— | C | =O | o-C$_6$H$_4$ | 3.0, 4.5 |
| 59 | 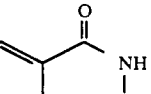 | VDM$^D$ | $NR^{14}$<br>$R^{14} = $ —NH(CO)— | C | =O | o-C$_6$H$_4$ | 2.9, 4.3 |
| 60 | 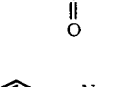 | VDM$^D$ | $NR^{14}$<br>$R^{14} = $ o-C$_6$H$_4$ | C | =NR$^{15}$<br>$R^{15}$ = sb to $X^1$ | H | 3.1, 4.6 |
| 61 | 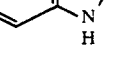 | VOX$^D$ | $NR^{14}$<br>$R^{14} = $ o-C$_6$H$_4$ | C | =NR$^{15}$<br>$R^{15}$ = sb to $X^1$ | H | E(50:50) |
| 62 | 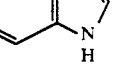 | VDM$^D$ | $NR^{14}$<br>$R^{14} = $ o-C$_6$H$_4$ | N | =NR$^{15}$<br>$R^{15}$ = sb to $X^1$ | ep | 3.2, 5.1 |
| 63 | 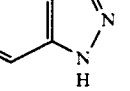 | VOX$^D$ | $NR^{14}$<br>$R^{14} = $ N=NNPh | C | =S | sb to $X^1$ | 3.0, 4.6 |
| 64 | 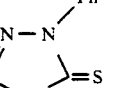 | VDM$^D$ | $NR^{14}$<br>$R^{14} = $ —N=C | N | =CR$^{15}$R$^{16}$<br>—R$^{15}$ =<br>$+$CH=CH$\frac{}{2}$<br>R$^{16}$ = sb to R$^{14}$ | ep to R$^{14}$ | 3.3, 5.1 |

EXAMPLES 65-67

The following examples were conducted with nitrogen heterocyclic compounds of Formula VIIId in which $p^1=p^2=q=1$. The resulting Formula VI Michael adducts were prepared using VDM as the Michael acceptor by the method of Example 45.

| Ex. | Michael Donor Formula VIIIa | AZLACTONE MICHAEL ADDUCT | | | | | | | Methylene Shifts |
|---|---|---|---|---|---|---|---|---|---|
| | | $X^1$ | $Z^1$ | $Y^1$ | G | $Y^2$ | $Z^2$ | $X^2$ | |
| 65$^A$ | 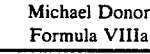 | $NR^{11}$<br>$R^{11} = $ o-C$_6$H$_4$ | | | $\begin{matrix} S \\ \parallel \\ [-C-] \end{matrix}$ | | | $NR^{11}$<br>$R^{11} = $ sb to $X^1$ | 3.1, 4.7 |

AZLACTONE MICHAEL ADDUCT

| Ex. | Michael Donor Formula VIIIa | $X^1$ | $Z^1$ | $Y^1$ | G | $Y^2$ | $Z^2$ | $X^2$ | Methylene Shifts |
|---|---|---|---|---|---|---|---|---|---|
| 66[B] | (benzimidazolone structure) | H | $NR^{11}$ $R^{11} = $ o-$C_6H_4$ | | $\overset{O}{\underset{[-C-]}{\|\|}}$ | | | $NR^{11}$ $R^{11} = $ sb to $X^1$ | 2.9, 4.3 |
| 67[A] | (Ph-substituted hydantoin-like structure with N—N, H H) | Ph | $NR^{11}$ $R^{11} = $ sb to $X^2$ | C | =O | Ph $\underset{-N-}{\|}$ | =O | C | $NR^{11}$ $R^{11} = $ sb to $X^1$ | 2.4, 3.8 |

EXAMPLE 68

This example teaches the Michael reaction of a 2-alkenyl azlactone and a Michael donor which contains different kinds or combinations of the Michael donors of the invention in that the barbituric acid structure contains both Formulae VIIIa and VIIIc linkages.

A slurry containing barbituric acid (89.60 grams; 0.70 mole) and VDM (389.20 grams; 2.80 moles) was warmed to 95° C. The result was a rather sudden warming to 195° C. and concomitant homogenization of the reaction mixture. The viscous liquid reaction mixture was maintained at 190° C. for 15 minutes and was then allowed to cool. The $^1$H-NMR spectrum of the resulting friable glassy material exhibited methylene resonances at $\delta$2.4, 2.6, 2.8, and 4.2 ppm.

EXAMPLES 69–71

Example 68 other compounds possessing multiple Michael donor linkages were prepared and are indicated with their relevant $^1$H-NMR shifts in TABLE VIII, below:

TABLE VIII

| Ex. | Compound | Formula VIII Components | Methylene Shifts |
|---|---|---|---|
| 69[B] | (indolinone structure) | VIII a & d | 2.0–2.4, 2.9, 4.1 |
| 70[A] | (dihydropyridinone structure) | VIII c & d | 2.7, 2.8, 4.1, 4.1 |
| 71[A] | (cyclic triamide structure) | VIII c & d | 2.8, 3.9 |

EXAMPLE 72

This example illustrates the utility of multi(azlactones) of the invention as crosslinking agents for polymeric coatings. Cellulose esters are well-known industrial polymers, often comprising the major polymeric ingredient of protective and decorative finishes on automobiles, furniture, metals, plastics, paper, and textiles. A principal disadvantage of these coatings or lacquers, as they are often called, is that their solvent resistance is either non-existent or poor.

Cellulose acetate propionate (available from the Eastman Kodak Co., Rochester, N.Y.) (hydroxyl equivalent weight=347) (1.71 grams; 0.00492 hydroxyl moles) was dissolved in ethyl acetate (15.39 grams). The tris(azlactone) of Example 71 (0.13 gram; 0.00025 mole) and DBU (0.013 gram) were added resulting in a slightly opalescent solution which remained relatively clear and non-turbid for about three hours. Meanwhile a portion of the solution was poured into an aluminum dish, and the solvent was removed and crosslinking was effected by heating at 80° C. for 20 minutes. The resulting polymeric film did not re-dissolve in ethyl acetate. Thus, the originally poorly solvent resistant cellulose ester on crosslinking with a multi-azlactone of the invention became solvent resistant.

EXAMPLE 73

This example demonstrates utilization of a monoazlactone-functional material of the invention to provide a covalent linkage between a polymer and a dye. In this example, the 2-alkenyl azlactone performs a coupling function between a Michael donor (the dye) and a hydroxy-functional polymer.

DBU (0.08 gram) was added to a solution containing poly(styrene-co-allyl alcohol) (RJ$^R$-101, available from Monsanto Corp., St. Louis, Mo.) (hydroxyl equivalent weight= 220) (0.88 gram; 0.004 hydroxyl moles), the reactive dye of Example 42 (1.60 grams, 0.003 mole), and ethyl acetate (3.72 grams) without incident. After heating at 70° C. for 19 h, IR indicated complete addition to the polymer had occurred. The Michael adduct copolymer solution was thrice precipitated into diethyl ether to produce a bright yellow powder.

Various modifications and alterations of this invention will become apparent to those skilled in the art without departing from the scope and spirit of this invention, and it should be understood that this invention is not to be unduly limited to the illustrative embodiments set forth herein.

We claim:

1. An azlactone-functional adduct having the formula

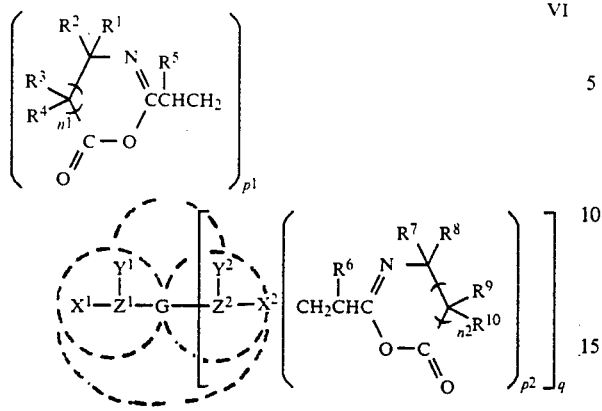

VI wherein
- $p^1$ and $p^2$ independently have integral values of 1 to (the valence of $X^1$ or $X^2$) $-1$, where $p^1$ relates to $X^1$ and $p^2$ to $X^2$;
- $R^1$, $R^2$, $R^7$, and $R^8$ independently represent an alkyl group, a cycloalkyl group, an aryl group, or at least one of ($R^1$ and $R^2$) and ($R^7$ and $R^8$) taken together with the carbon atom to which they are joined form a ring of 4 to 12 atoms;
- $R^3$, $R^4$, $R^9$, and $R^{10}$ are independently hydrogen or lower alkyl;
- $R^5$ and $R^6$ independently are hydrogen or methyl;
- $n^1$ and $n^2$ independently are 0 or 1;
- $X^1$ and $X^2$ independently are selected from the group consisting of —$CH_2$ (when at least one of $p^1$ and $p^2=1$); —CH (when at least one of $p^1$ and $p^2=2$); —C (when at least one of $p^1$ and $p^2=3$); —$CR^{11}R^{12}$ in which $R^{11}$ and $R^{12}$ are selected from the group consisting of alkyl, alkenyl, cycloalkyl, and aryl monovalent groups, a single bond, and polyvalent alkylene, alkenylene, cycloalkylene, or arylene linking groups; —$CHR^{11}$; —$CR^{11}$; —$CW^1W^2$ in which $W^1$ and $W^2$ are independently selected from $R^{11}O_2C$—, $R^{11}(CO)$—, $N\equiv C$—, $R_F(CO)$— in which $R_F$ is a substantially perfluorinated alkyl, cycloalkyl, or aryl group, $R^{11}NH(CO)$—, $R^{11}R^{12}N(CO)$—, $R^{11}SO_2$—, $R^{11}R^{12}C=N$—, $R^{11}N=(R^{12})C$—, $R^{11}(CS)$—, $R^{11}S_2C$—, $R^{11}NH(CS)$—, $R^{11}R^{12}N(CS)$—, $R^{11}R^{12}C=CR^{13}$— in which $R^{13}$ is defined the same as $R^{11}$ and $R^{12}$, and $O_2N$— groups; —$CR^{11}W^1$; —$CHW^1$; —$CW^1$; —$NR^{14}$ in which $R^{14}$ (linking at least one of $X^1$ to $Y^1$, $X^1$ to G, $X^1$ to $X^2$, $X^2$ to $Y^2$, and $X^2$ to G) is a single bond, alkylene, alkenylene, or arylene group such that the ring formed contains 4 to 6 ring atoms; and —$NW^1$;
- $Z^1$ and $Z^2$ independently are C, N, or S=O;
- $Y^1$ and $Y^2$ independently are doubly bonded oxygen (=O); doubly bonded sulfur (=S); =$CR^{15}R^{16}$, or —$CR^{15}=CR^{16}R^{17}$ in which $R^{15}$ and $R^{16}$ independently are defined the same as $R^{11}$, $R^{12}$, and $R^{13}$, except that $R^{15}$ can be an electron pair, and in which $R^{17}$ is a monovalent group selected from alkyl, alkenyl, cycloalkyl, and aryl groups; =$NR^{15}$ (to include triply bonded nitrogen (≡N:) when $R^{15}$ is an electron pair and G is a single bond from at least one of $Y^1$ to $Z^1$ and $Y^2$ to $Z^2$); or —$NR^{18}R^{19}$ in which $R^{18}$ and $R^{19}$ independently can be hydrogen, alkyl, cycloalkyl, aryl, a single bond, alkylene, cycloalkylene, or arylene, or together with the nitrogen atom to which they are joined form a ring of 4 to 12 ring atoms; and
- G is —H; —$NR^{20}R^{21}$ in which $R^{20}$ and $R^{21}$ independently are defined the same as $R^{11}$, $R^{12}$, and $R^{13}$; —$NHR^{20}$; —$R^{20}$; or —$OR^{20}$; =O; polymeric monovalent and polyvalent groups; an electron pair; or a single bond; and
- q is an integer of zero or greater and is equal to (the valence of G)$-1$; wherein said azlactone-functional adduct is prepared by a process comprising the step of reacting at least one 2-alkenyl azlactone Michael acceptor of Formulae VIIa and VIIb:

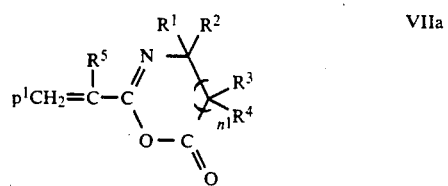

VIIa and

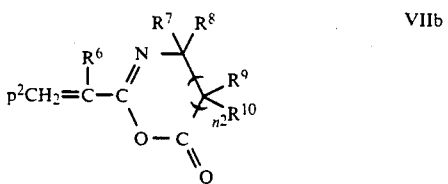

VIIb wherein:
$R^1$, $R^2$, $R^3$, $R^4$, $R^5$, $R^6$, $R^7$, $R^8$, $R^9$, $R^{10}$, $n^1$, $n^2$, $p^1$, and $p^2$ are as previously defined,
with a Michael donor of Formula VIII

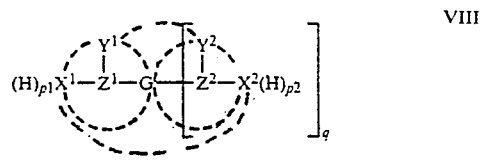

VIII wherein
$X^1$, $X^2$, $Y^1$, $Y^2$, $Z^1$, $Z^2$, G, q, $p^1$ and $p^2$ are as previously defined, to provide said azlactone-functional adduct.

2. An azlactone-functional adduct having the formula

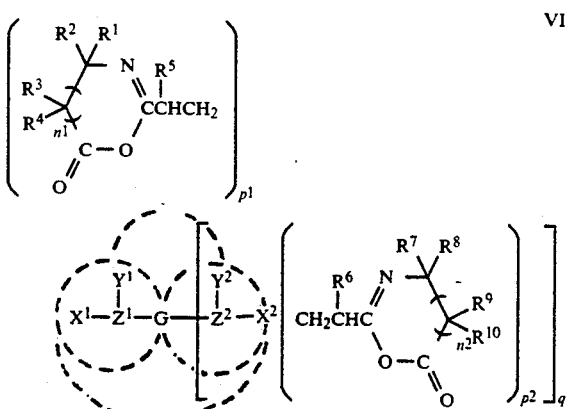

VI wherein p$^1$ and p$^2$ independently have integral values of 1 to (the valence of X$^1$ or X$^2$) −1, where p$^1$ relates to X$^1$ and p$^2$ to X$^2$;

R$^1$, R$^2$, R$^7$, and R$^8$ independently represent an alkyl group, a cycloalkyl group, an aryl group, or at least one of (R$^1$ and R$^2$) and (R$^7$ and R$^8$) taken together with the carbon atom to which they are joined form a ring of 4 to 12 atoms;

R$^3$, R$^4$, R$^9$, and R$^{10}$ are independently hydrogen or lower alkyl;

R$^5$ and R$^6$ independently are hydrogen or methyl;

n$^1$ and n$^2$ independently are 0 or 1;

X$^1$ and X$^2$ independently are selected from the group consisting of —CH$_2$ (when at least one of p$^1$ and p$^2$=1); —CH (when at least one of p$^1$ and p$^2$=2); —C (when at least one of p$^1$ and p$^2$=3); —CR$^{11}$R$^{12}$ in which R$^{11}$ and R$^{12}$ are selected from the group consisting of alkyl, alkenyl cycloalkyl, and aryl monovalent groups; a single bond; and polyvalent alkylene, alkenylene, cycloalkylene, or arylene linking groups; —CHR$^{11}$; —CR$^{11}$; —CW$^1$W$^2$ in which W$^1$ and W$^2$ are independently selected from R$^{11}$O$_2$C—, R$^{11}$(CO)—, N≡C—, R$_F$(CO)— in which R$_F$ is a substantially perfluorinated alkyl, cycloalkyl, or aryl group, R$^{11}$NH(CO)—, R$^{11}$R$^{12}$N(CO)—, R$^{11}$SO$_2$—, R$^{11}$R$^{12}$C=N—, R$^{11}$N=(R$^{12}$)C—, R$^{11}$(CS)—, R$^{11}$S$_2$C—, R$^{11}$NJ(CS)—, R$^{11}$R$^{12}$N(CS)—, R$^{11}$R$^{12}$C=CR$^{13}$— in which R$^{13}$ is defined the same as R$^{11}$ and R$^{12}$, and O$_2$N— groups; —CR$^{11}$W$^1$; —CHW$^1$; —CW$^1$; —NR$^{14}$ in which R$^{14}$ (linking at least one of X$^1$ to Y$^1$, X$^1$ to G, X$^1$ to X$^2$, X$^2$ to Y$^2$, and X$^2$ to G) is a single bond, alkylene, alkenylene, or arylene group such that the ring formed contains 4 to 6 ring atoms; and —NW$^1$;

Z$^1$ and Z$^2$ independently are C;

Y$^1$ and Y$^2$ independently are doubly bonded oxygen (=O) doubly bonded sulfur (=S); =CR$^{15}$R$^{16}$, or —CR$^{15}$=CR$^{16}$R$^{17}$ in which R$^{15}$ and R$^{16}$ independently are defined the same as R$^{11}$, R$^{12}$, and R$^{13}$, except that R$^{15}$ can be an electron pair, and in which R$^{17}$ is a monovalent group selected from alkyl, alkenyl, cycloalkyl, and aryl groups; =NR$^{15}$ (to include triply bonded nitrogen (≡N:) when R$^{15}$ is an electron pair and G is a single bond from at least one of Y$^1$ to Z$^1$ and Y$^2$ to Z$^2$); or —NR$^{18}$R$^{19}$ in which R$^{18}$ and R$^{19}$ independently can be hydrogen, alkyl, cycloalkyl, aryl, a single bond, alkylene, cycloalkylene, or arylene, or together with the nitrogen atom to which they are joined form a ring of 4 to 12 ring atoms;

G is —H; —NR$^{20}$R$^{21}$ in which R$^{20}$ and R$^{21}$ independently are defined the same as R$^{11}$, R$^{12}$, and R$^{13}$; —NHR$^{20}$; —R$^{20}$; or —OR$^{20}$; =O; polymeric monovalent and polyvalent groups; an electron pair; or a single bond; and q is an integer of 0 or greater and is equal to (the valence of G)−1.

3. The adduct according to claim 2 wherein

X$^1$ and X$^2$ independently are —CH$_2$; —CH; —C; —CR$^{11}$R$^{12}$; —CHR$^{11}$; —CR$^{11}$; —CW$^1$W$^2$; —CR$^{11}$W$^1$; —CHW$^1$; or —CW$^1$; in which R$^{11}$, R$^{12}$, W$^1$ and W$^2$ are as previously defined;

Y$^1$ and Y$^2$ independently are doubly bonded oxygen (=O); doubly bonded sulfur (=S); =CR$^{15}$R$^{16}$; or =NR$^{15}$; in which R$^{15}$ and R$^{16}$ are as previously defined; and Z$^1$, Z$^2$, G, q, p$^1$, and p$^2$ are as previously defined.

4. The adduct according to claim 2 wherein

X$^1$ and X$^2$ independently are —C, —CH, —CR$^{11}$, or —CHR$^{11}$ in which R$^{11}$ is as previously defined;

Z$^1$ and Z$^2$ are C;

Y$^1$ and Y$^2$ independently are —CR$^{15}$=CR$^{16}$R$^{17}$ or —NR$^{18}$R$^{19}$, in which R$^{15}$, R$^{16}$, R$^{17}$, R$^{18}$, and R$^{19}$ are as previously defined; and G, q, p$^1$ and p$^2$ are as previously defined.

5. The adduct according to claim 2 wherein

X$^1$ and X$^2$ independently are —NW$^1$ in which W$^1$ is as previously defined;

Z$^1$ and Z$^2$ independently are C;

Y$^1$ and Y$^2$ independently are doubly bonded oxygen (=O); doubly bonded sulfur (=S); or =NR$^{15}$ in which R$^{15}$ is as previously defined; and G, q, p$^1$, and p$^2$ are as previously defined.

6. The adduct according to claim 2 wherein

X$^1$ and X$^2$ independently are —NR$^{14}$ in which R$^{14}$ is as previously defined;

Z$^1$ and Z$^2$ independently are C, N;

Y$^1$ and Y$^2$ independently are doubly bonded oxygen (=O); doubly bonded sulfur (=S); =CR$^{15}$R$^{16}$; or =NR$^{15}$; in which R$^{15}$ and R$^{16}$ are as previously defined; and G, q, p$^1$ and p$^2$ are as previously defined.

7. The adduct according to claim 2 wherein

G contains one or more of S, O, N, P, halogen, and Si atoms.

8. The adduct according to claim 2 wherein

G includes at least one functional group selected from the group consisting of alkyl, alkenyl, aryl, amide, thioamide, ester, thioester, ketone, thioketone, nitrile, nitro, sulfide, sulfoxide, disulfide, tertiary amine, ether, urethane, dithiocarbamate, quaternary ammonium, phosphonium, halogen, silyl, and silyloxy.

9. The adduct according to claim 2 wherein G is monovalent.

10. The adduct according to claim 2 wherein G is polyvalent.

11. The adduct according to claim 2 which is a precursor to an adhesive.

12. The adduct according to claim 2 which is a precursor to a sealant.

13. The adduct according to claim 2 which is a precursor to a coating.

* * * * *

UNITED STATES PATENT AND TRADEMARK OFFICE
CERTIFICATE OF CORRECTION

PATENT NO. : 5,149,806
DATED : September 22, 1992
INVENTOR(S) : Dean M. Moren et al.

It is certified that error appears in the above-indentified patent and that said Letters Patent is hereby corrected as shown below:

Col. 6, line 21, "0" should be -- O --.

Cols. 6 and 7, replace Scheme I with the following:

--

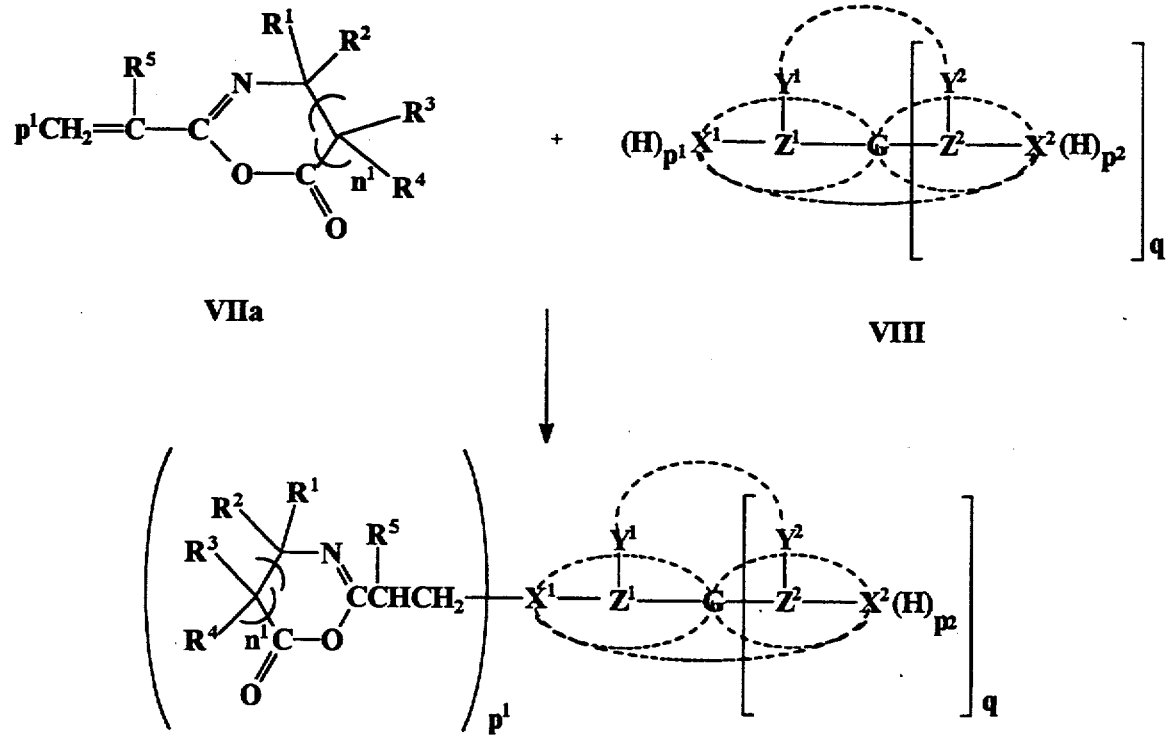

UNITED STATES PATENT AND TRADEMARK OFFICE
CERTIFICATE OF CORRECTION

PATENT NO. : 5,149,806
DATED : September 22, 1992
INVENTOR(S) : Dean M. Moren et al.

It is certified that error appears in the above-indentified patent and that said Letters Patent is hereby corrected as shown below:

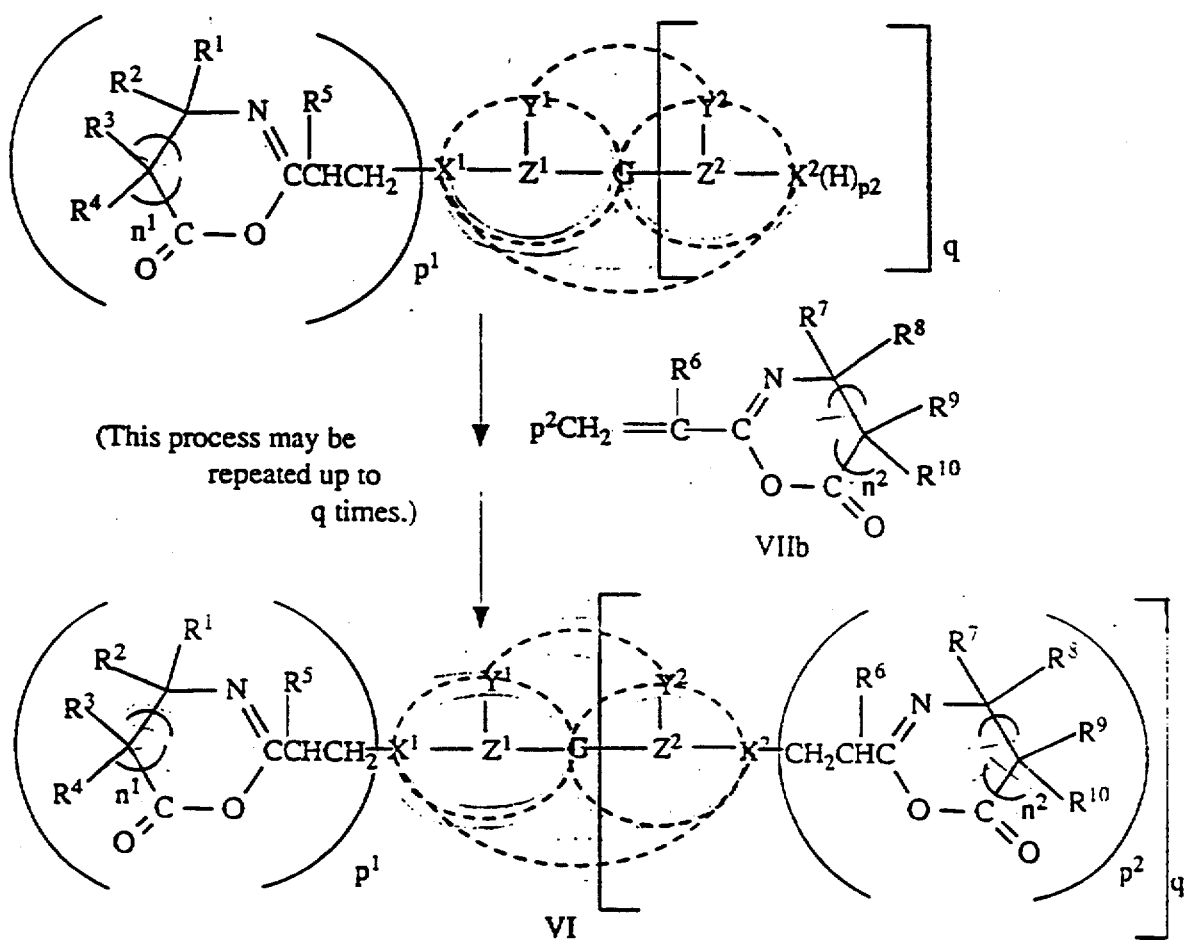

(This process may be repeated up to q times.)

UNITED STATES PATENT AND TRADEMARK OFFICE
CERTIFICATE OF CORRECTION

PATENT NO. : 5,149,806
DATED : September 22, 1992
INVENTOR(S) : Dean M. Moren et al.

It is certified that error appears in the above-indentified patent and that said Letters Patent is hereby corrected as shown below:

Col. 7, lines 36-37, "2-vinyl-4-ethyl-4-methyl-2-oxazolin 5-one" should read -- 2-vinyl-4-ethyl-4-methyl-2-oxazolin-5-one --.

Col. 7, lines 37-38, "2-vinyl 4,4-dimethyl-1,3-oxazolin-6-one" should read -- 2-vinyl-4,4-dimethyl-1,3-oxazolin-6-one --.

Cols. 8 and 9, replace Scheme II with the following: --

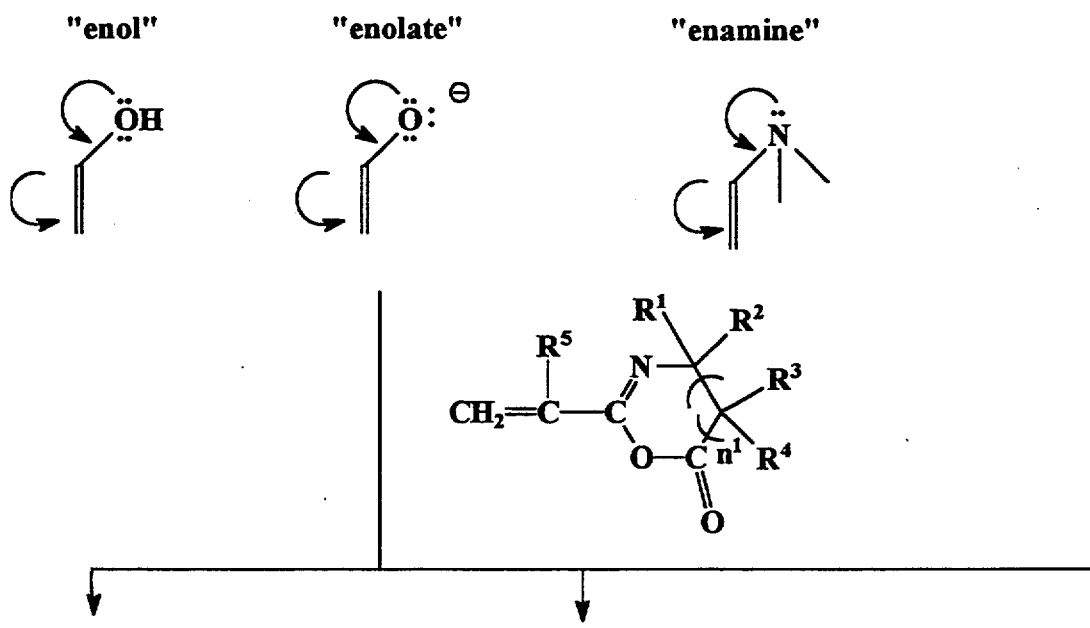

UNITED STATES PATENT AND TRADEMARK OFFICE
CERTIFICATE OF CORRECTION

PATENT NO. : 5,149,806

DATED : September 22, 1992

INVENTOR(S) : Dean M. Moren et al.

It is certified that error appears in the above-indentified patent and that said Letters Patent is hereby corrected as shown below:

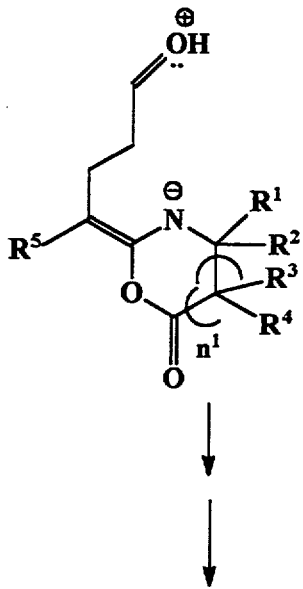 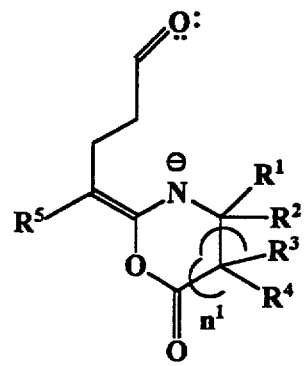 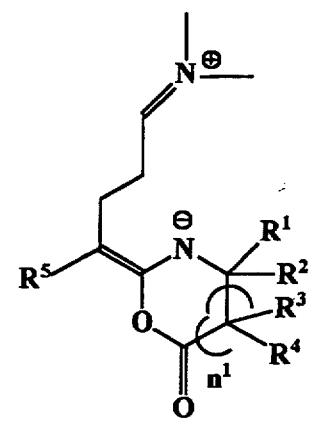

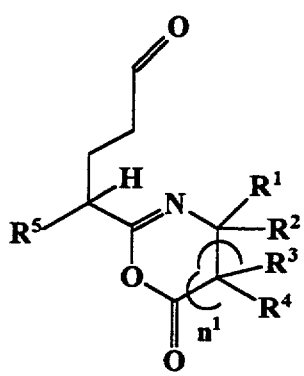 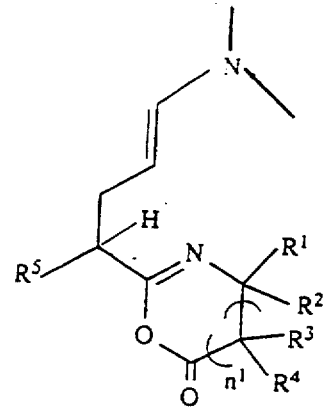

UNITED STATES PATENT AND TRADEMARK OFFICE
CERTIFICATE OF CORRECTION

PATENT NO. : 5,149,806

DATED : September 22, 1992

INVENTOR(S) : Dean M. Moren et al.

It is certified that error appears in the above-identified patent and that said Letters Patent is hereby corrected as shown below:

Col. 9, lines 37-45, replace "$K^2$" in formula VIIIa with -- $X^2$ --.

Col. 11, lines 9-14, there should be a double bond connecting the "O" at line 10 to the structure.

Col. 12, line 51, after "following" insert

Col. 13, lines 17-34, replace structures IXa and IXb with the following:

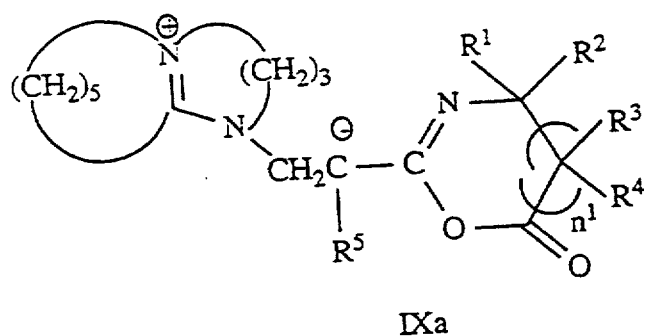

IXa

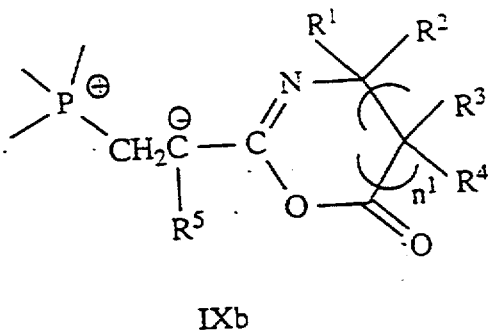

IXb

UNITED STATES PATENT AND TRADEMARK OFFICE
CERTIFICATE OF CORRECTION

PATENT NO. : 5,149,806
DATED : September 22, 1992
INVENTOR(S) : Dean M. Moren et al.

It is certified that error appears in the above-indentified patent and that said Letters Patent is hereby corrected as shown below:

Col. 16, line 5, "nitro9en" should read -- nitrogen --.

Col. 16, lines 12-18, replace formula VIIIc with the following:

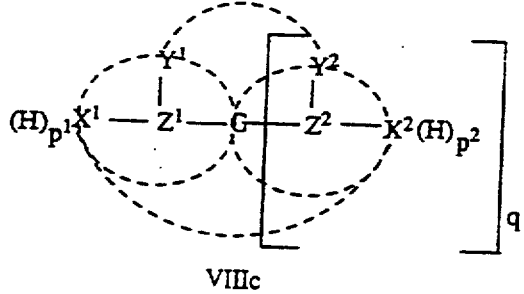

VIIIc

Col. 17, line 19, after "spectra" insert -- . --.

Col. 17, lines 22-28, replace formula VIIId with the following:

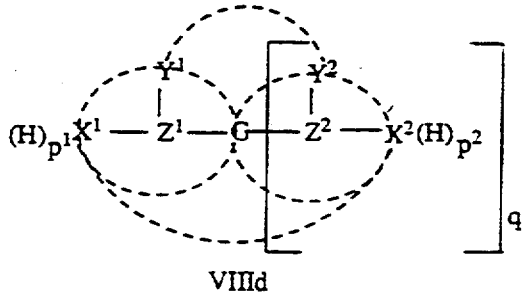

VIIId

UNITED STATES PATENT AND TRADEMARK OFFICE
CERTIFICATE OF CORRECTION

PATENT NO. : 5,149,806

DATED : September 22, 1992

INVENTOR(S) : Dean M. Moren et al.

It is certified that error appears in the above-indentified patent and that said Letters Patent is hereby corrected as shown below:

Col. 20, line 37, "H-NMR" should read -- $^1$H-NMR --.

Col. 20, line 41, "$n^1 = O$" should read -- $n^1 = 0$ --.

Col. 20, line 45, "$n^1 = O$" should read -- $n^1 = 0$ --.

Col. 20, line 50, "$n^1 = O$" should read -- $n^1 = 0$ --.

Cols. 23-24, Table III, for Example 28, under column "$Z^1$" insert -- [ --; under column "G" delete the brackets; under column "$Z^2$" insert -- ] --.

Cols. 23-24, Table III, for Example 29, under column "$Z^1$" insert -- [ --; under column "G" delete the brackets; under column "$Z^2$" insert -- ] --.

Cols. 23-24, Table IV, for Example 33, under column "$Z^1$" insert -- [ --; under column "G" delete the brackets; under column "$Z^2$" insert -- ] --.

Cols. 23-24, Table IV, for Example 34, under column "$Z^1$" insert -- [ --; under column "G" delete the brackets; under column "$Z^2$" insert -- ] --.

Col. 26, line 59, "H-NMR" should read -- $^1$H-NMR --.

Cols. 27-28, Table V, in the column headings, line 3, on the far right side, "$X^1CHCHR^5$" should read -- $X^1CH_2CHR^5$ --.

UNITED STATES PATENT AND TRADEMARK OFFICE
CERTIFICATE OF CORRECTION

PATENT NO. : 5,149,806
DATED : September 22, 1992
INVENTOR(S) : Dean M. Moren et al.

It is certified that error appears in the above-indentified patent and that said Letters Patent is hereby corrected as shown below:

Table V, in the entry for Example 42, under col. "$W^1$", "$C_6H_4$ = NPh" should read -- $C_6H_4N$ = NPh --.

Col. 28, line 46, "which $^1$ = 1" should read -- which $p^1$ = 1 --.

In the table at the bottom of cols. 31-32, for Example 65, under column "$Z^1$" insert -- [ --; under column "G" delete the brackets; under column $Z^2$ insert -- ] --.

In the table at the top of cols. 33-34, for Example 66, under column "$Z^1$" insert -- [ --; under column "G" delete the brackets; under column $Z^2$ insert -- ] --.

Col. 33, line 36, before "Example 68" insert -- In the manner of --.

Col. 35, line 55, delete ", N, or S = O".

Col. 37, line 29, "$R^{11}NJ(CS)$" should read -- $R^{11}NH(CS)$ --.

UNITED STATES PATENT AND TRADEMARK OFFICE
CERTIFICATE OF CORRECTION

PATENT NO. : 5,149,806
DATED : September 22, 1992
INVENTOR(S): Dean M. Moren et al.

It is certified that error appears in the above-indentified patent and that said Letters Patent is hereby corrected as shown below:

Col. 37, line 40, after "(=O)" insert -- ; --.

Col. 38, line 32, "are C,N;" should read -- are C; --.

Signed and Sealed this

Fourth Day of July, 1995

BRUCE LEHMAN

Attest:

*Attesting Officer*   *Commissioner of Patents and Trademarks*